US012564417B2

(12) United States Patent
Shelton, IV et al.

(10) Patent No.: US 12,564,417 B2
(45) Date of Patent: Mar. 3, 2026

(54) SURGICAL INSTRUMENT WITH VARIOUS ALIGNMENT FEATURES AND METHOD FOR IMPROVED DISASSEMBLY AND ASSEMBLY

(71) Applicant: Cilag GmbH International, Zug (CH)

(72) Inventors: Frederick E. Shelton, IV, Hillsboro, OH (US); Jacqueline C. Aronhalt, Loveland, OH (US); Rebecca Spatholt, Cincinnati, OH (US); Ellen Burkart, Cincinnati, OH (US); Robert N. Carranza, Milford, OH (US)

(73) Assignee: Cilag GmbH International, Zug (CH)

( * ) Notice: Subject to any disclaimer, the term of this patent is extended or adjusted under 35 U.S.C. 154(b) by 703 days.

(21) Appl. No.: 17/854,120

(22) Filed: Jun. 30, 2022

(65) Prior Publication Data

US 2024/0000475 A1 Jan. 4, 2024

(51) Int. Cl.
*A61B 17/32* (2006.01)
*A61B 34/30* (2016.01)

(52) U.S. Cl.
CPC ...... *A61B 17/320092* (2013.01); *A61B 34/30* (2016.02); *A61B 2034/306* (2016.02)

(58) Field of Classification Search
CPC ............ A61B 17/320092; A61B 34/30; A61B 2034/306; A61B 2017/00477; A61B 18/12
See application file for complete search history.

(56) References Cited

U.S. PATENT DOCUMENTS

| | | |
|---|---|---|
| 5,374,813 A | 12/1994 | Shipp |
| 7,354,440 B2 | 4/2008 | Truckai et al. |
| 7,381,209 B2 | 6/2008 | Truckai et al. |

(Continued)

FOREIGN PATENT DOCUMENTS

| | | |
|---|---|---|
| CN | 202682045 U | 1/2013 |
| CN | 102909184 A | 2/2013 |

(Continued)

OTHER PUBLICATIONS

U.S. Appl. No. 17/854,110.

(Continued)

*Primary Examiner* — Linda C Dvorak
*Assistant Examiner* — William Mossbrook
(74) *Attorney, Agent, or Firm* — FBT Gibbons LLP

(57) ABSTRACT

A surgical instrument including an end effector that may transition between a deactivated and activated configured to transmit energy to tissue, and a proximal body attached to the end effector. The proximal body includes an electrical component that may assist the end effector, a first shroud, and a second shroud capable of coupling with the first shroud to cooperatively define a hollow interior that houses the electrical component. The proximal body further includes a first restraining feature and a second restraining feature associated with the first shroud and the second shroud, respectively. The first and second restraining features may couple together to cooperatively align the first shroud and the second shroud. The first and second restraining feature may selectively disengage to allow the first shroud and the second shroud to decouple form each other and expose the electrical component within the hollow interior.

6 Claims, 24 Drawing Sheets

(56) References Cited

U.S. PATENT DOCUMENTS

| | | | | |
|---|---|---|---|---|
| 8,319,134 B2 * | 11/2012 | Blomeyer | .......... | A61B 18/1402 |
| | | | | 606/49 |
| 8,663,220 B2 | 3/2014 | Wiener et al. | | |
| 8,820,605 B2 | 9/2014 | Shelton, IV | | |
| 9,125,662 B2 | 9/2015 | Shelton, IV | | |
| 9,314,308 B2 | 4/2016 | Parihar et al. | | |
| 9,949,785 B2 | 4/2018 | Price et al. | | |
| 10,624,709 B2 | 4/2020 | Remm | | |
| 10,835,307 B2 | 11/2020 | Shelton, IV et al. | | |
| 11,229,471 B2 | 1/2022 | Shelton, IV et al. | | |
| 11,690,642 B2 | 7/2023 | Black et al. | | |
| 2006/0079874 A1 | 4/2006 | Faller et al. | | |
| 2007/0191713 A1 | 8/2007 | Eichmann et al. | | |
| 2008/0200940 A1 | 8/2008 | Eichmann et al. | | |
| 2011/0300010 A1 * | 12/2011 | Jarnagin | ............ | A61B 17/3207 |
| | | | | 417/477.2 |
| 2012/0111591 A1 | 5/2012 | Shelton, IV et al. | | |
| 2012/0115005 A1 | 5/2012 | Stulen et al. | | |
| 2012/0116380 A1 | 5/2012 | Madan et al. | | |
| 2012/0292367 A1 | 11/2012 | Morgan et al. | | |
| 2013/0009606 A1 | 1/2013 | Smith et al. | | |
| 2015/0148829 A1 * | 5/2015 | Kimball | ......... | A61B 17/320068 |
| | | | | 606/169 |
| 2017/0000515 A1 * | 1/2017 | Akagane | .................. | A61N 7/02 |
| 2019/0201046 A1 | 7/2019 | Shelton, IV et al. | | |
| 2019/0201077 A1 | 7/2019 | Yates et al. | | |
| 2019/0201080 A1 | 7/2019 | Messerly et al. | | |
| 2019/0201091 A1 | 7/2019 | Yates et al. | | |
| 2019/0207857 A1 | 7/2019 | Shelton, IV et al. | | |
| 2019/0274717 A1 | 9/2019 | Nott et al. | | |
| 2019/0311802 A1 | 10/2019 | Kokubo et al. | | |
| 2020/0078114 A1 | 3/2020 | Asher et al. | | |
| 2020/0297973 A1 | 9/2020 | Blacker et al. | | |
| 2021/0284406 A1 | 9/2021 | McDonald | | |
| 2023/0013884 A1 | 1/2023 | Yardibi et al. | | |

FOREIGN PATENT DOCUMENTS

| | | | | | |
|---|---|---|---|---|---|
| CN | 105559879 A | | 5/2016 | | |
| DE | 202015105781 U1 | * | 12/2015 | ....... | A61B 17/00234 |
| EP | 3593744 A1 | * | 1/2020 | ......... | A61B 17/0218 |
| JP | 2014180498 A | * | 9/2014 | | |
| WO | WO-2012131672 A4 | * | 2/2013 | ............ | A61H 23/00 |
| WO | WO 2016/118196 A1 | | 7/2016 | | |
| WO | WO 2021/059210 A1 | | 4/2021 | | |

OTHER PUBLICATIONS

U.S. Appl. No. 17/854,114; and.

U.S. Appl. No. 17/854,127.

International Search Report and Written Opinion dated Oct. 23, 2023, for International Application No. PCT/IB2023/056625, 14 pages.

International Search Report and Written Opinion dated Aug. 30, 2023, for International Application No. PCT/IB2023/056627, 16 pages.

International Search Report and Written Opinion dated Oct. 30, 2023, for International Application No. PCT/IB2023/056634, 21 pages.

International Search Report and Written Opinion dated Sep. 1, 2023, for International Application No. PCT/IB2023/056636, 14 pages.

U.S. Appl. No. 62/611,339 entitled "Robot Assisted Surgical Platform," filed Dec. 28, 2017.

U.S. Appl. No. 62/611,340 entitled "Cloud-Based Medical Analytics," filed Dec. 28, 2017.

U.S. Appl. No. 62/611,341 entitled "Interactive Surgical Platform," filed Dec. 28, 2017.

U.S. Appl. No. 17/854,050 entitled, "Surgical Instrument with Predetermined Separation Feature for Waste Stream Utilization and Related Methods," filed Jun. 30, 2022.

U.S. Appl. No. 17/854,065 entitled, "Method of Reclaiming Portions of Surgical Instruments for Remanufacturing and Sustainability," filed Jun. 30, 2022.

U.S. Appl. No. 17/854,104 entitled, "Robotic Surgical System with Removable Portion and Method of Disassembling Same," filed Jun. 30, 2022.

U.S. Appl. No. 17/854,110 entitled, "System for Determining Disposal of Surgical Instrument and Related Methods," filed Jun. 30, 2022.

U.S. Appl. No. 17/854,114 entitled, "Reclamation Packaging for Surgical Instrument and Related Methods," filed Jun. 30, 2022.

U.S. Appl. No. 17/854,127 entitled, "Surgical System and Methods for Instrument Assessment and Cleaning," filed Jun. 30, 2022.

U.S. Appl. No. 17/854,166 entitled, "Surgical Instrument with Removable Cable and Associated Couplings," filed Jun. 30, 2022.

U.S. Appl. No. 17/854,641 entitled, "Surgical System and Methods of Assembly and Disassembly of Surgical Instrument," filed Jun. 30, 2022.

* cited by examiner

102

135 — MONITOR

138 — IMAGING MODULE    106

140 — GENERATOR MODULE

142 — MONOPOLAR

144 — BIPOLAR

146 — ULTRASONIC

126 — SMOKE EVACUATION MODULE

128 — SUCTION/IRRIGATION MODULE

130 — COMMUNICATION MODULE

132 — PROCESSOR MODULE

134 — STORAGE ARRAY

133 — OPERATING ROOM MAPPING MODULE    136

VISUALIZATION SYSTEM 108

ROBOTIC SYSTEM 110

INTELLIGENT INSTRUMENT 112

147

148

146

145

154

139

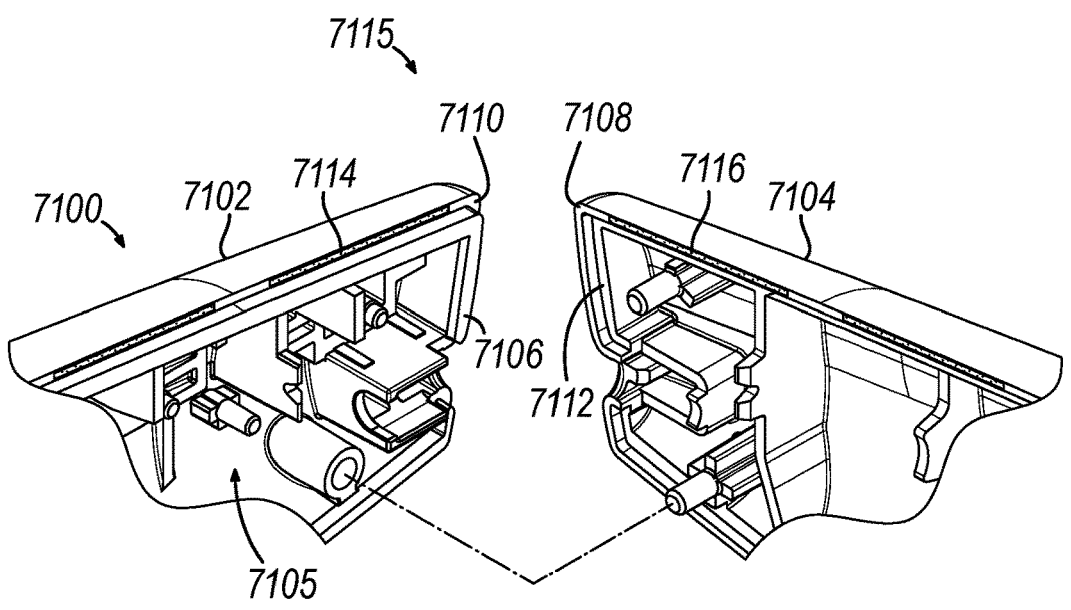
FIG. 12
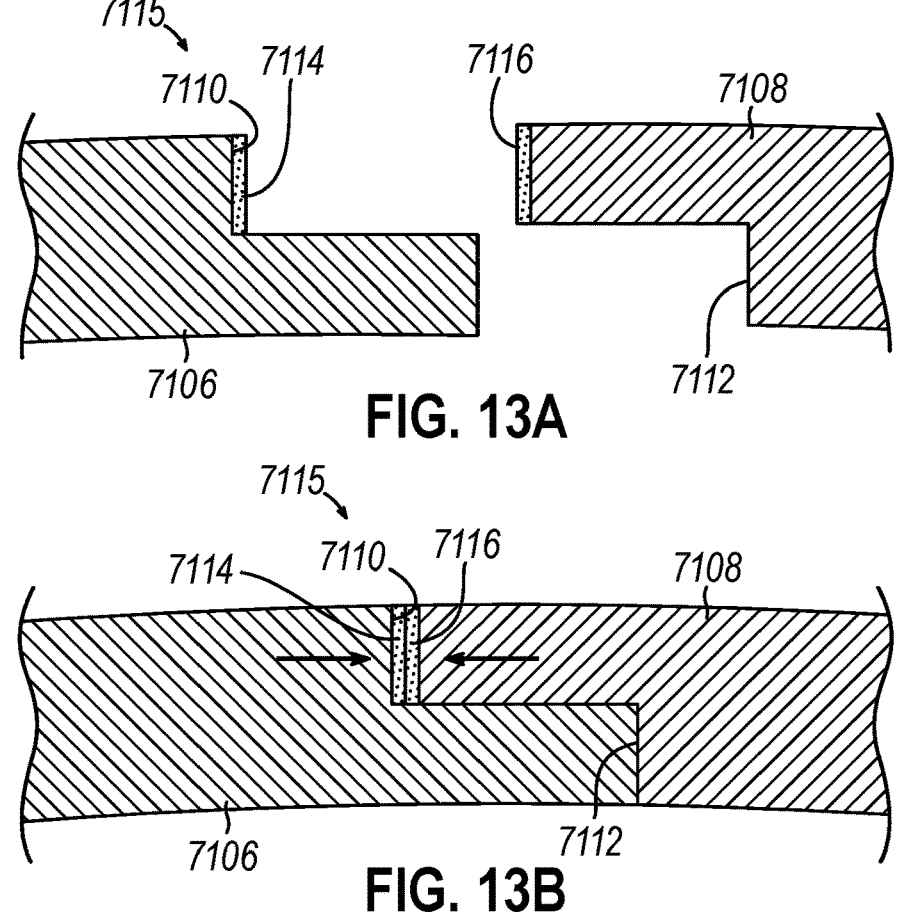
FIG. 13A
FIG. 13B

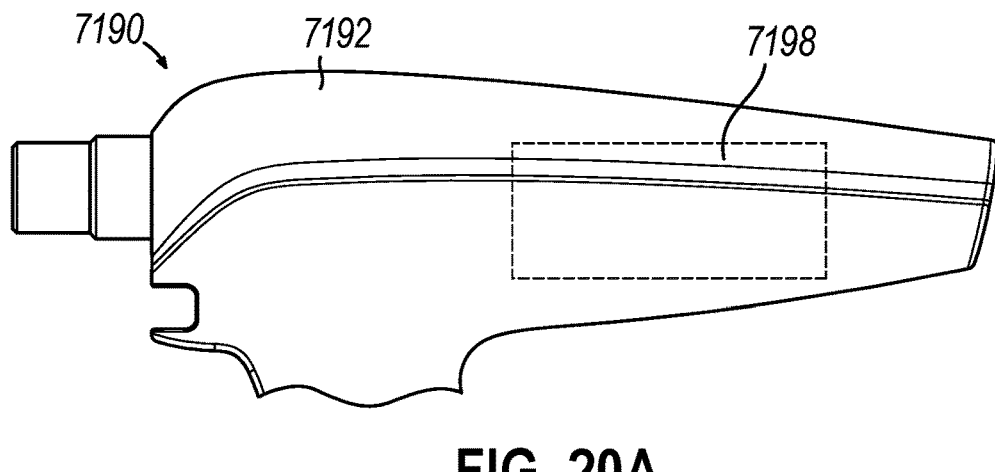
FIG. 20A
FIG. 20B
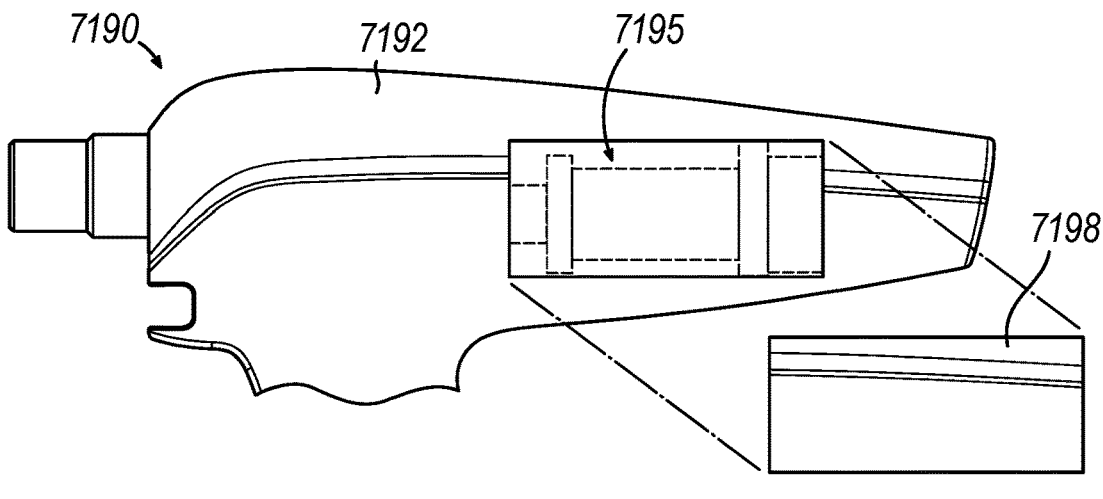
FIG. 20C

7200

7202

7204

7206

7200

7202

7204

7206

INTERACTIVE DEVICE

7208

7200

7202

7204

7206

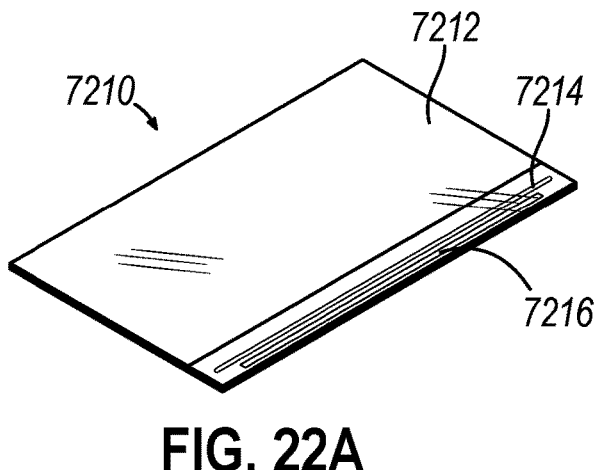
FIG. 22A
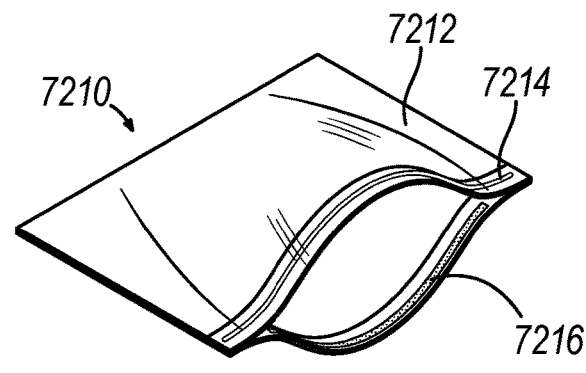
FIG. 22B
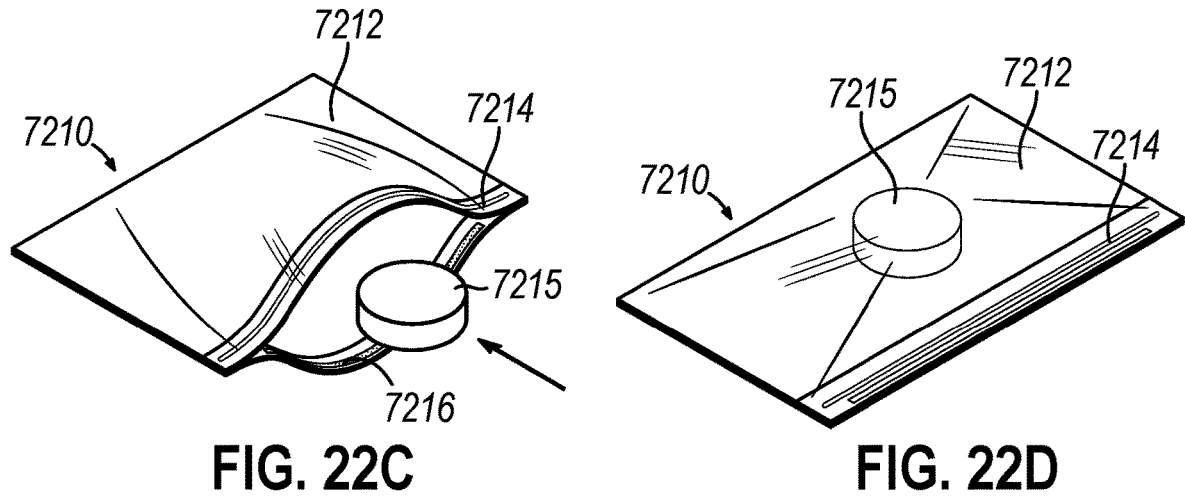
FIG. 22C            FIG. 22D

SURGICAL INSTRUMENT WITH VARIOUS ALIGNMENT FEATURES AND METHOD FOR IMPROVED DISASSEMBLY AND ASSEMBLY

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; U.S. Pat. No. 8,663,220, entitled "Ultrasonic Electrosurgical Instruments," issued Mar. 4, 2014, the disclosure of which is incorporated by reference herein, in its entirety; U.S. Pat. No. 10,835,307, entitled "Modular Battery Powered Handheld Surgical Instrument Containing Elongated Multi-Layered Shaft," issued Nov. 17, 2020, the disclosure of which is incorporated by reference herein, in its entirety; and U.S. Pat. No. 11,229,471, entitled "Modular Battery Powered Handheld Surgical Instrument with Selective Application of Energy Based on Tissue Characterization," issued January 25, 2022, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," published on May 2, 2019, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat.

No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023, the disclosure of which is incorporated by reference herein, in its entirety.

Such instruments and robotic surgical systems may be further be incorporated into a surgical system for performing procedures in a surgical environment, such as surgical operating theaters or rooms in a healthcare facility. A sterile field is typically created around the patient and may include properly attired, scrubbed healthcare professions as well as desired furniture and/or fixtures. Examples of such surgical systems and associated features are disclosed in U.S. Pat. Pub. No. 2019/0201046, entitled "Method for Controlling Smart Energy Devices," published on Jul. 4, 2019, issued as U.S. Pat. No. 11,589,888 on Feb. 28, 2023, the disclosure of which is incorporated by reference herein, in its entirety; U.S. Pat. Pub. No. 2019/0201080, entitled "Ultrasonic Energy Device Which Varies Pressure Applied by Clamp Arm to Provide Threshold Control Pressure at a Cut Progression Location," published on Jul. 4, 2019, issued as U.S. Pat. No. 11,419,667 on Aug. 23, 2022, the disclosure of which is incorporated by reference herein, in its entirety; U.S. Pat. Pub. No. 2019/0201091, entitled "Radio Frequency Energy Device for Delivering Combined Electrical Signals," published Jul. 4, 2019, issued as U.S. Pat. No. 11,364,075 on Jun. 21, 2022, the disclosure of which is incorporated by reference herein, in its entirety; U.S. Pat. Pub. No. 2019/0274717, entitled "Methods for Controlling Temperature in Ultrasonic Device," published Sep. 12, 2019, issued as U.S. Pat. No. 11,259,830 on Mar. 1, 2022, the disclosure of which is incorporated by reference herein, in its entirety; and U.S. Pat. Pub. No. 2019/0207857, entitled "Surgical Network Determination of Prioritization of Communication, Interaction, or Processing Based on System or Device Needs," published Jul. 4, 2019, issued as U.S. Pat. No. 10,892,995 on Jan. 12, 2021, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts an enlarged exploded perspective view of another exemplary proximal body that may be readily incorporated into any of the surgical instruments shown herein;

FIG. 13A depicts an enlarged sectional of a coupling assembly of the proximal body of FIG. 12 in a decoupled configuration;

FIG. 13B depicts an enlarged sectional view of the coupling assembly of FIG. 13A in a coupled configuration;

FIG. 20A depicts an enlarged elevational side view of another exemplary proximal body that may be readily incorporated into any of the surgical instruments shown herein;

FIG. 20B depicts an enlarged elevational side view of the proximal body of FIG. 20A, where a heat source is hovered over the proximal body;

FIG. 20C depicts an enlarged elevational side view of the proximal body of FIG. 20A, where a hatch door of the proximal body is removed;

FIG. 22A depicts a perspective view of a processing bag assembly in a closed configuration;

FIG. 22B depicts a perspective view of the processing bag assembly of FIG. 22A in an open configuration;

FIG. 22C depicts a perspective view of the processing bag assembly of FIG. 22A in the open configuration with a surgical component loaded therein;

FIG. 22D depicts a perspective view of the processing bag assembly of FIG. 22A in the closed configuration with the surgical component of FIG. 22C loaded therein;

Figure 1:
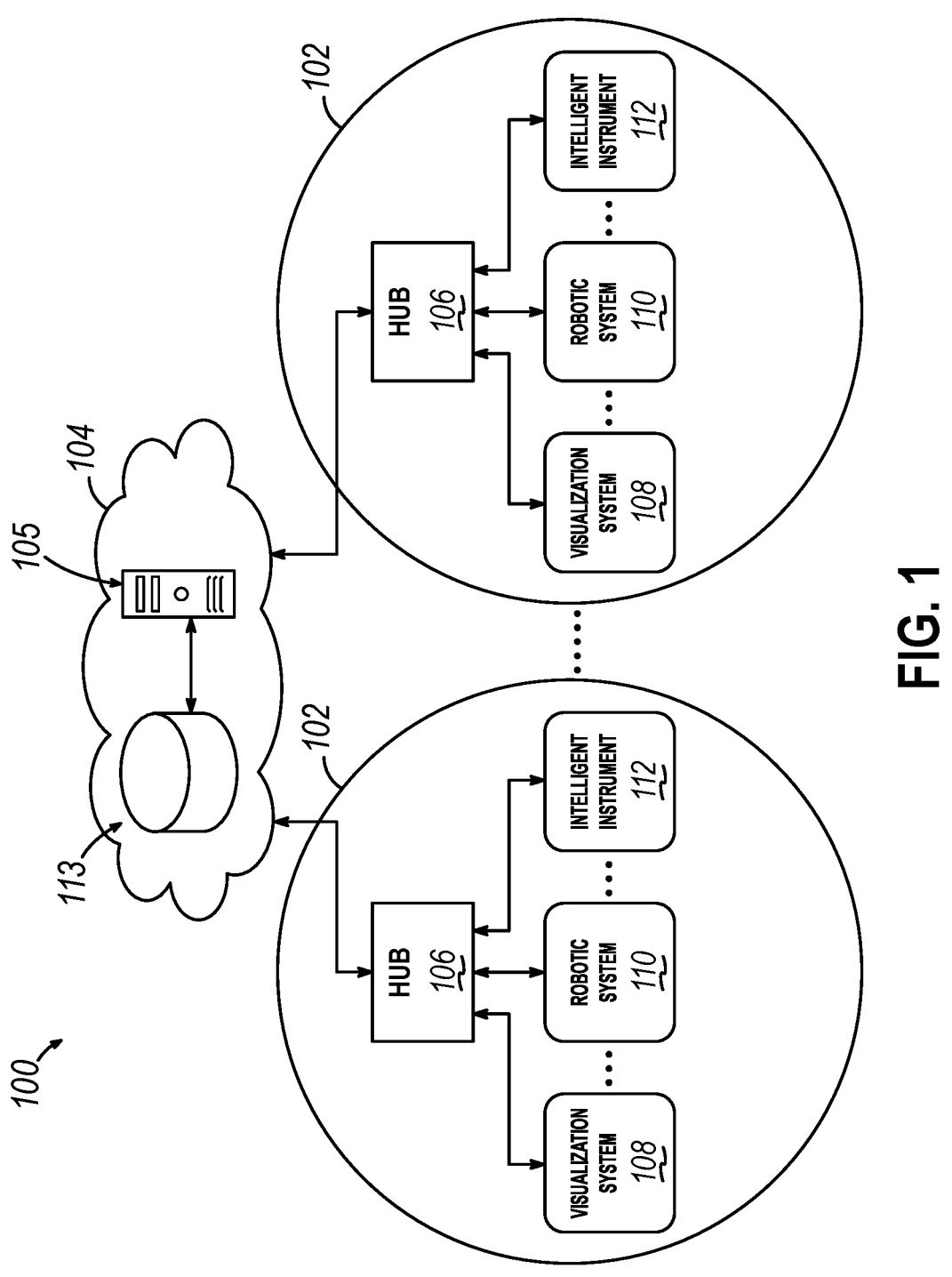
FIG. 1 depicts a block diagram of an example a computer-implemented interactive surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. EXAMPLE OF A SURGICAL SYSTEM

With respect to FIG. 1, a computer-implemented interactive surgical system (100) includes one or more surgical systems (102) and a cloud-based system (e.g., a cloud (104) that may include a remote server (113) coupled to a storage device (105)). Each surgical system (102) of the present example includes at least one surgical hub (106) in communication with cloud (104) that may include a remote server (113). In one example, as illustrated in FIG. 1, surgical system (102) includes a visualization system (108), a robotic system (110), and a handheld intelligent surgical instrument (112), which are configured to communicate with one another and/or hub (106). In some aspects, a surgical system (102) may include an M number of hubs (106), an N number of visualization systems (108), an O number of robotic systems (110), and a P number of handheld intelligent surgical instruments (112), where M, N, O, and P are integers greater than or equal to one. In any case, any suitable combination of features provided below may be incorporated into an exemplary surgical system, such as surgical system (100), and used in the surgical theater in order to perform a desired surgical procedure as would be apparent to one skilled in the art in view of the teachings herein.

Figure 2:
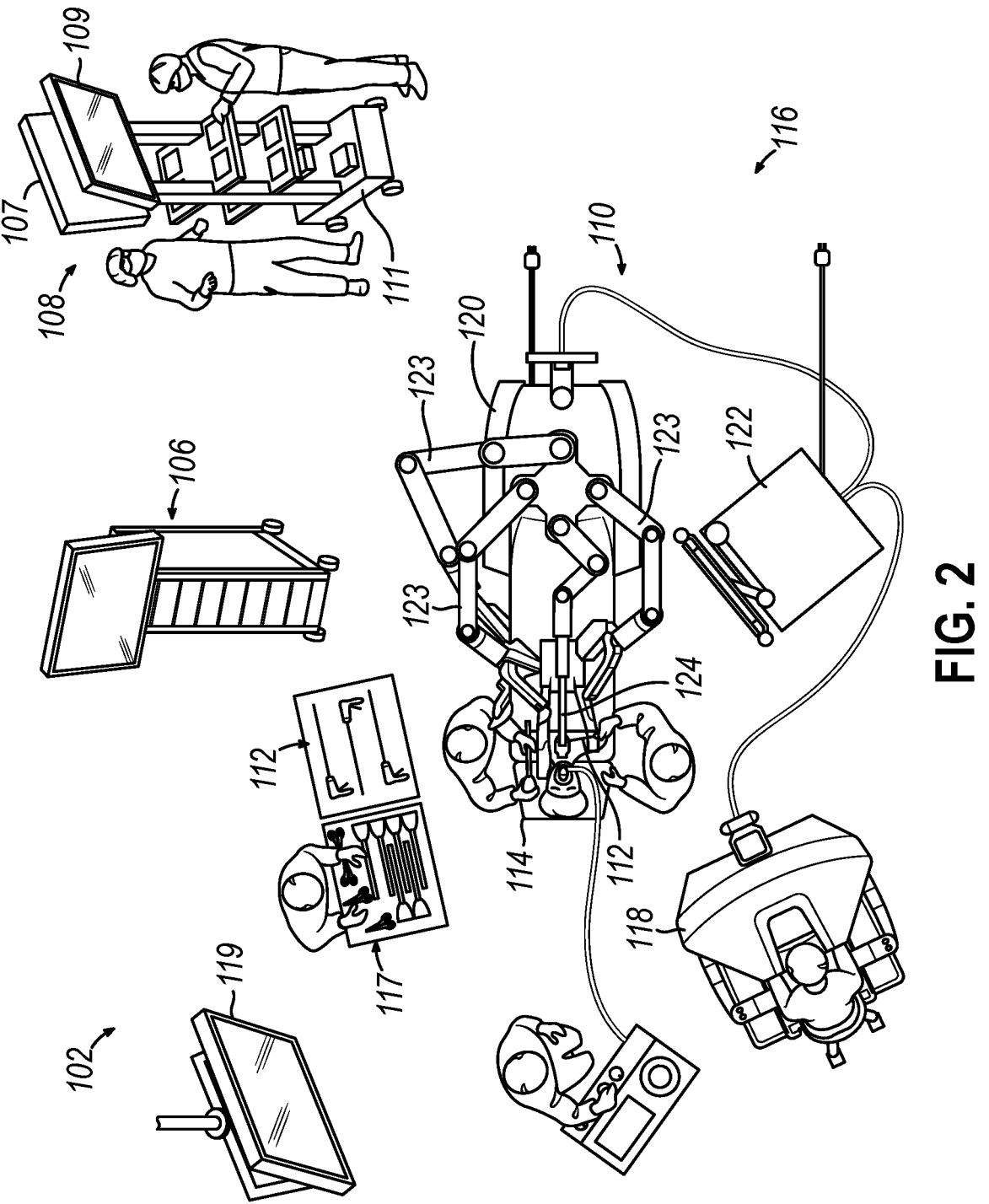
FIG. 2 depicts a top schematic view of an example of a surgical system for performing a surgical procedure in an operating room of a healthcare facility.

FIG. 2 depicts an example of a surgical system (102) being used to perform a surgical procedure on a patient who is lying down on an operating table (114) in a surgical operating room (116). A robotic system (110) is used in the surgical procedure as a part of surgical system (102). Robotic system (110) includes a surgeon's console (118), a patient side cart (120) (surgical robot), and a surgical robotic hub (122). Patient side cart (120) can manipulate at least one removably coupled surgical tool (117) with any one of a plurality of surgical arms (123) through a minimally invasive incision in the body of the patient while the surgeon views the surgical site through console (118). An image of the surgical site can be obtained by a medical imaging device (124), which can be manipulated by patient side cart (120) to orient imaging device (124). Robotic hub (122) can be used to process the images of the surgical site for subsequent display to the surgeon through console (118).

Other types of robotic systems can be readily adapted for use with surgical system (102). Various examples of robotic systems and surgical tools that are suitable for use with the present disclosure are described in U.S. Provisional Patent Application Ser. No. 62/611,339, entitled "Robot Assisted Surgical Platform," filed Dec. 28, 2017, the disclosure of which is herein incorporated by reference in its entirety.

Various examples of cloud-based analytics that are performed by cloud (104, and are suitable for use with the present disclosure, are described in U.S. Provisional Patent Application Ser. No. 62/611,340, entitled Cloud-Based Medical Analytics," filed Dec. 28, 2017, the disclosure of which is herein incorporated by reference in its entirety.

In various aspects, imaging device (124) includes at least one image sensor and one or more optical components. Suitable image sensors include, but are not limited to, Charge-Coupled Device (CCD) sensors and Complementary Metal-Oxide Semiconductor (CMOS) sensors. In various aspects, imaging device (124) is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. Some aspects of spectral and multi-spectral imaging are described in greater detail under the heading "Advanced Imaging Acquisition Module" in U.S. Provisional Patent Application Ser. No. 62/611,341, entitled "Interactive Surgical Platform," filed Dec. 28, 2017, the disclosure of which is herein incorporated by reference in its entirety.

Strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In addition to the introduction of any features of surgical system (100), furniture, or fixtures into the sterile field requiring sterilization, additional complications may result from removal of these features from the sterile field, particularly when such features may have contacted, or presumed to have contacted, the patient, including any tissues and/or fluids associated with the surgical procedure. Such contamination of these features from the patient often requires special consideration during or after the surgical procedure, particularly when processing these features for disposal, reuse, or remanufacturing as desired. In one example, surgical system (100) and/or healthcare professionals associated with the surgical procedure may be specifically equipped to address such processing as discussed below in greater detail.

As illustrated in FIG. 2, a primary display (119) is positioned in the sterile field to be visible to an operator at operating table (114). In addition, a visualization tower (111) is positioned outside the sterile field. Visualization tower (111) includes a first non-sterile display (107) and a second non-sterile display (109), which face away from each other. Visualization system (108), guided by hub (106), is configured to utilize displays (107, 109, 119) to coordinate information flow to operators inside and outside the sterile field. For example, hub (106) may cause visualization system (108) to display a snapshot of a surgical site, as recorded by imaging device (124), on a non-sterile display (107) or (109), while maintaining a live feed of the surgical site on the primary display (119). The snapshot on non-sterile display (107) or display (109) can permit a non-sterile operator to perform a diagnostic step relevant to the surgical procedure, for example.

In one aspect, hub (106) is also configured to route a diagnostic input or feedback entered by a non-sterile operator at visualization tower (111) to primary display (119) within the sterile field, where it can be viewed by a sterile operator at the operating table. In one example, the input can be in the form of a modification to the snapshot displayed on non-sterile display (107) or display (109), which can be routed to primary display (119) by hub (106).

Referring to FIG. 2, a surgical instrument (112) is being used in the surgical procedure as part of surgical system (102). Hub (106) is also configured to coordinate information flow to a display of the surgical instrument (112) such as in, for example, U.S. Provisional Patent Application Ser. No. 62/611,341, entitled "Interactive Surgical Platform," filed Dec. 28, 2017, the disclosure of which is herein incorporated by reference in its entirety. A diagnostic input or feedback entered by a non-sterile operator at visualization tower (111) can be routed by hub (106) to surgical instrument display (115) within the sterile field, where it can be viewed by the operator of surgical instrument (112). Example surgical instruments that are suitable for use with surgical system (102) are described under the heading "Surgical Instrument Hardware" and in U.S. Provisional Patent Application Ser. No. 62/611,341, entitled "Interactive Surgical Platform," filed Dec. 28, 2017, the disclosure of which is herein incorporated by reference in its entirety, for example.

Figure 3:
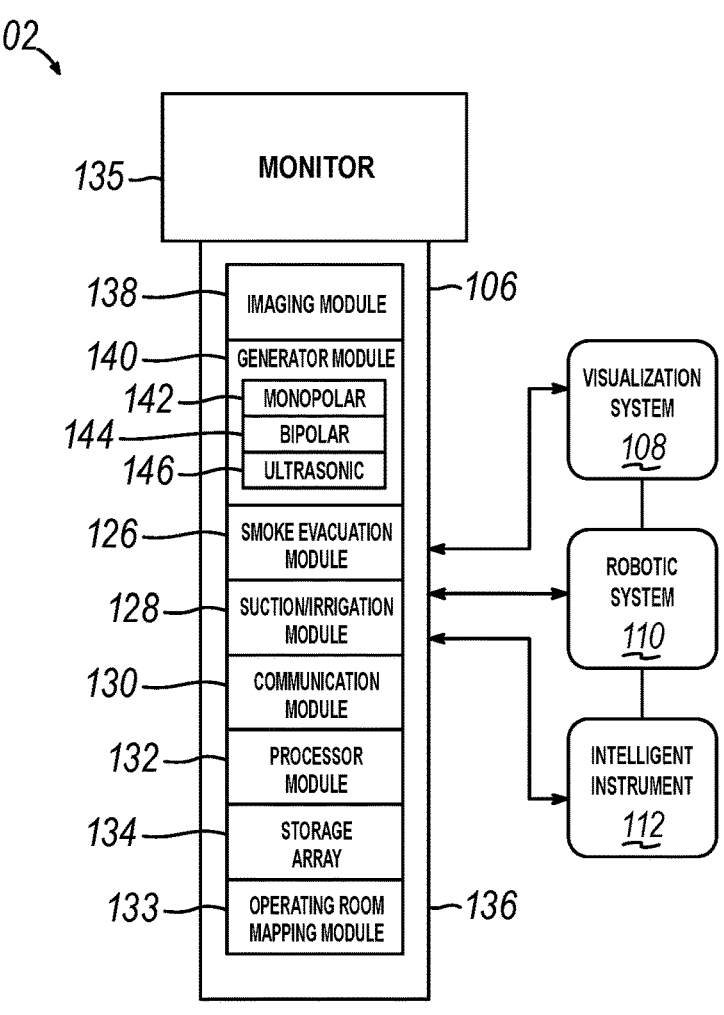
FIG. 3 depicts a side schematic view of an example of a surgical hub of the surgical system of FIG. 2.

Referring now to FIG. 3, a hub (106) is depicted in communication with a visualization system (108), a robotic system (110), and a handheld intelligent surgical instrument (112). Hub (106) includes a hub display (135), an imaging module (138), a generator module (140), a communication module (130), a processor module (132), and a storage array (134). In certain aspects, as illustrated in FIG. 3, hub (106) further includes a smoke evacuation module (126), a suction/irrigation module (128), and/or an operating room mapping module (133).

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure (136) offers a unified environment for managing the power, data, and fluid lines, which reduces the frequency of entanglement between such lines.

Figure 4:
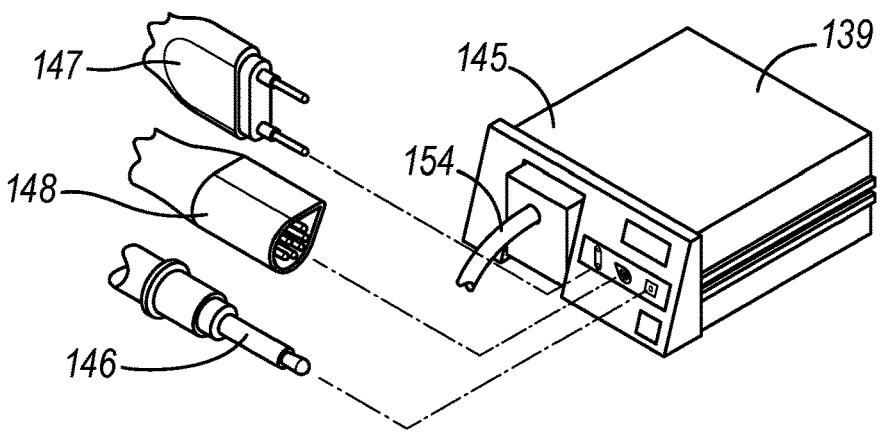
FIG. 4 depicts a perspective view of a combination generator module with bipolar, ultrasonic, and monopolar contacts of the surgical system of FIG. 2.

Referring to FIGS. 3-4, aspects of the present disclosure are presented for a hub modular enclosure (136) that allows the modular integration of a generator module (140), a smoke evacuation module (126), and a suction/irrigation module (128). Hub modular enclosure (136) further facilitates interactive communication between modules (140, 126, 128). As shown in FIG. 4, generator module (140) can be a generator module with integrated monopolar, bipolar, and ultrasonic components supported in a single housing unit (139) slidably insertable into hub modular enclosure (136). As illustrated in FIG. 4, generator module (140) can be configured to connect to a monopolar device (146), a bipolar device (147), and an ultrasonic device (148). Alternatively, generator module (140) may comprise a series of monopolar, bipolar, and/or ultrasonic generator modules that interact through hub modular enclosure (136). Hub modular enclosure (136) can be configured to facilitate the insertion of multiple generators and interactive communication between the generators docked into the hub modular enclosure (136) so that the generators would act as a single generator.

Figure 5:
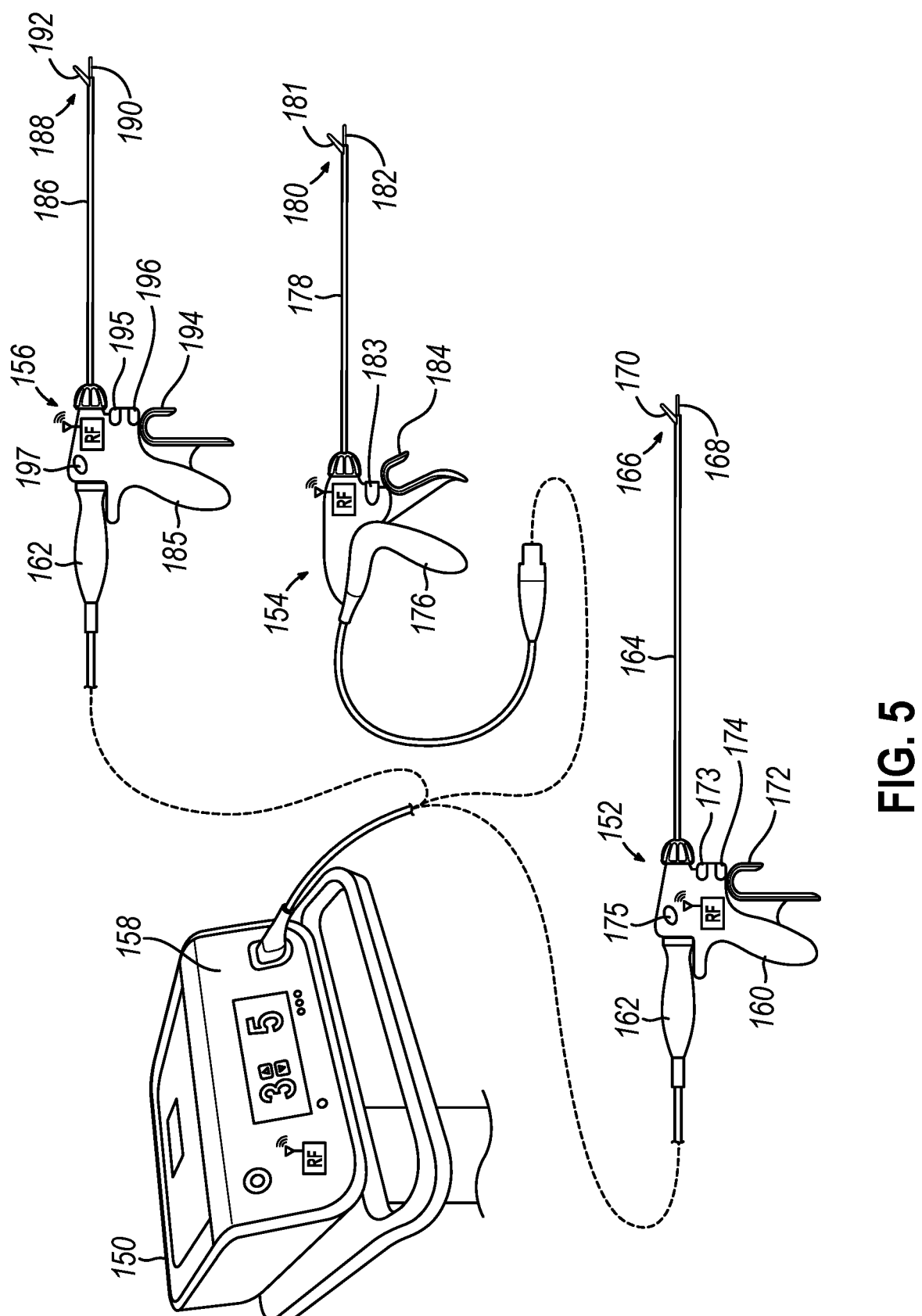
FIG. 5 depicts a side schematic view of an exemplary generator and various examples of surgical instruments for use with the surgical system of FIG. 2.

FIG. 5 illustrates one form of a generator (150) and various surgical instruments (152, 154, 156) usable therewith, where surgical instrument (152) is an ultrasonic surgical instrument (152), surgical instrument (154) is an RF electrosurgical instrument (154), and multifunction surgical instrument (156) is a combination ultrasonic/RF electrosurgical instrument (156). Generator (150) is configurable for use with a variety of surgical instruments. According to various forms, generator (150) may be configurable for use with different surgical instruments of different types including, for example, ultrasonic surgical instruments (152), RF electrosurgical instruments (154), and multifunction surgical instruments (156) that integrate RF and ultrasonic energies delivered simultaneously from generator (150). Although generator (150) of the present example in FIG. 5 is shown separate from surgical instruments (152, 154, 156), generator (150) may alternatively be formed integrally with any of surgical instruments (152, 154, 156) to form a unitary surgical system. Generator (150) comprises an input device (158) located on a front panel of generator (150) console. Input device (158) may comprise any suitable device that generates signals suitable for programming the operation of generator (150). Generator (150) may be configured for wired or wireless communication.

Generator (150) of the present example is configured to drive multiple surgical instruments (152, 154, 156). One example of such surgical instrument is ultrasonic surgical instrument (152) and comprises a handpiece (160), an ultrasonic transducer (162), a shaft assembly (164), and an end effector (166). End effector (166) includes an ultrasonic blade (168) acoustically coupled to ultrasonic transducer (162) and a clamp arm (170). Handpiece (160) has a trigger (172) to operate clamp arm (170) and a combination of toggle buttons (173, 174, 175) to energize and drive ultrasonic blade (168) or other function. Toggle buttons (173, 174, 175) can be configured to energize ultrasonic transducer (162) with generator (150).

Generator (150) also is configured to drive another example of surgical instrument (154). RF electrosurgical instrument (154) includes a handpiece (176), a shaft assembly (178), and an end effector (180). End effector (180) includes electrodes in clamp arms (181, 182) and return through an electrical conductor portion of shaft assembly (178). Electrodes are coupled to and energized by a bipolar energy source within generator (150). Handpiece (176) includes a trigger (183) to operate clamp arms (181, 182) and an energy button (184) to actuate an energy switch to energize electrodes in end effector (180).

Generator (150) also is configured to drive multifunction surgical instrument (156). Multifunction surgical instrument (156) includes a handpiece (185), a shaft assembly (186), and an end effector (188). End effector (188) has an ultrasonic blade (190) and a clamp arm (192). Ultrasonic blade (190) is acoustically coupled to ultrasonic transducer (162). Handpiece (185) has a trigger (194) to operate clamp arm (192) and a combination of toggle buttons (195, 196, 197) to energize and drive ultrasonic blade (190) or other function. Toggle buttons (195, 196, 197) can be configured to energize ultrasonic transducer (162) with generator (150) and energize ultrasonic blade (190) with a bipolar energy source also contained within generator (150). It will be appreciated that handpieces (160, 176, 185) may be replaced with a robotically controlled instrument for incorporating one or more aspects of surgical instruments (152, 154, 156). Accordingly, the term "handpiece" should not be limited to this context and to handheld use.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions, all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferro-electric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device. Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

II. EXEMPLARY SURGICAL INSTRUMENT WITH ALIGNMENT FEATURES FOR IMPROVED ASSEMBLY AND DISASSEMBLY

As mentioned above, objects intended to penetrate a sterile field of the surgical theater during a surgical procedure need to be suitably sterilized; while objects leaving the sterile field after a surgical procedure often require special consideration when processing for disposal, reuse, or remanufacturing. In some instances, surgical instrument/tool (112, 117, 152, 154, 156) may require at least some degree of assembly within the surgical theater prior to exemplary use in accordance with the description herein; and then require some degree of disassembly after exemplary use such that selective components may be harvested for disposal, reuse, and/or remanufacturing. Therefore, in some instances, a surgical instrument/tool (112, 117, 152, 154, 156) may be introduced into the sterile field as a surgical kit with subcomponents requiring at least some degree of assembly prior to exemplary use. In addition to the subcomponents used to form surgical instrument/tool (112, 117, 152, 154, 156), such a surgical kit may contain tools for assembly, disassembly, and suitable processing for disposal, reuse, or remanufacturing of instrument/tool (112, 117, 152, 154, 156) and its subcomponents.

In some instances, a proximal body of surgical instrument/tool (112, 117, 152, 154, 156), such as handpiece (160, 176, 185), may contain internal components (such as electronics and/or batteries) that need be processed for disposal, reuse, or remanufacturing separately from the rest of handpiece (160, 176, 185). Therefore, such internal components may need to be accessed and removed from handpiece (160, 176, 185) after a surgical procedure, but within the sterile surgical theater.

It may be desirable to provide a proximal body, such as handpiece (160, 176, 185), with internal components that are accessible within the surgical theater. However, it is also desirable to ensure the proximal body, such as handpiece (160, 176, 185), is structurally robust enough to maintain its assembled formation during exemplary use of surgical instrument/tool (112, 117, 152, 154, 156). In other words, it may be desirable to selectively access internal components of handpiece (160, 176, 185) after exemplary use in a surgical procedure; yet also ensure handpiece (160, 176, 185) does not inadvertently disassemble during exemplary use in a surgical procedure.

Figure 6:
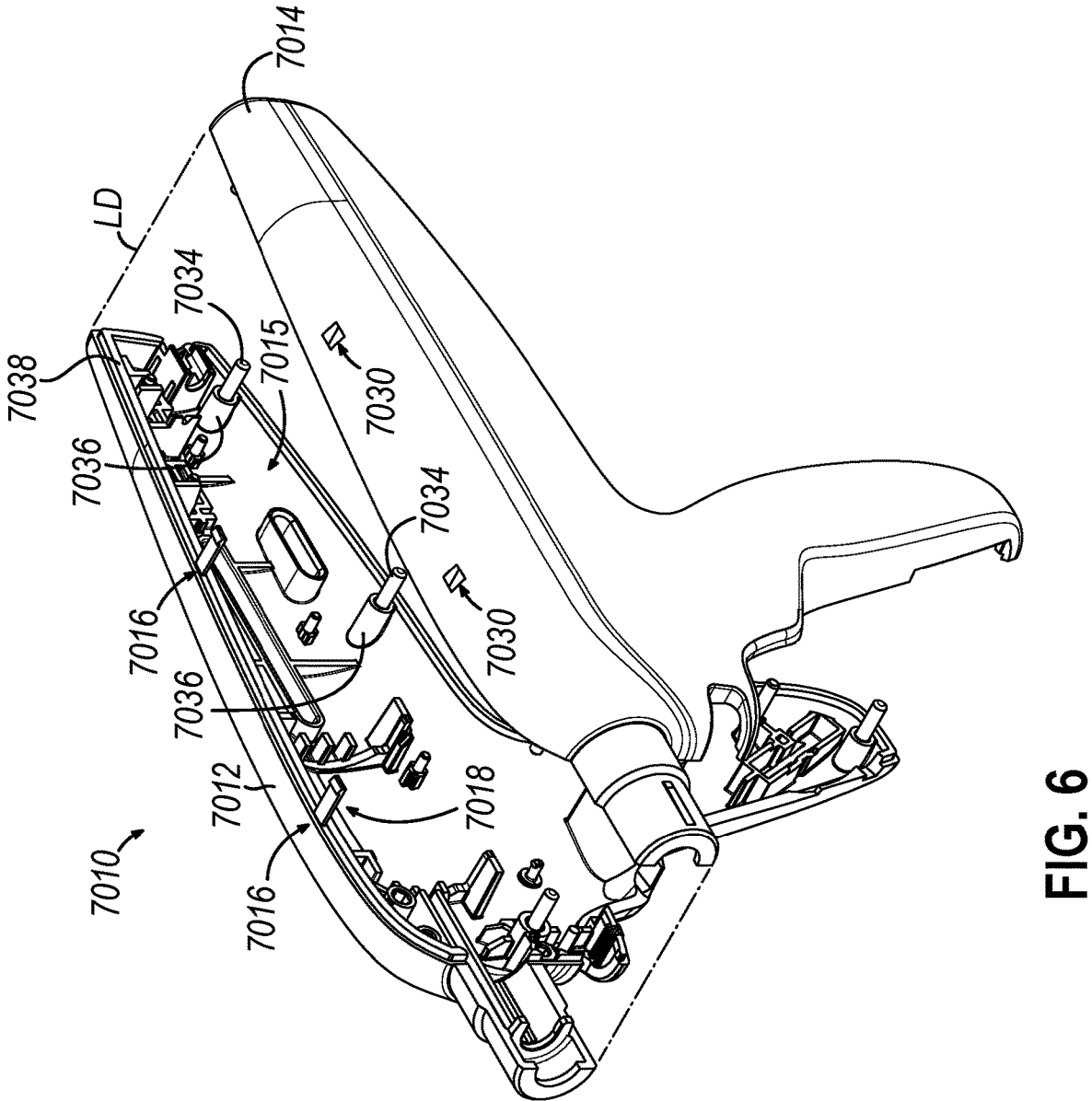
FIG. 6 depicts an exploded perspective view of an exemplary proximal body that may be readily incorporated into any of the surgical instruments shown herein.

FIG. 6 shows an exemplary proximal body (7010) that may be readily incorporated into surgical instrument/tool (112, 117, 152, 154, 156). Proximal body (7010) includes a first shroud (7012) and a second shroud (7014) that are configured to couple together in order to form proximal body (7010). As will be described in greater detail below, first shroud (7012) and second shroud (7014) contain complementary coupling features configured to resist inadvertent disassembly of proximal body (7010) during exemplary use, but also allow a user to separate shroud (7012, 7014) after exemplary use in order to harvest internal components for processing.

In the current example, proximal body (7010) is shown as a handpiece, such that proximal body (7010) may be used in replacement of handpiece (160, 176, 185) described above. Proximal body (7010) is configured to suitably couple with a shaft assembly and end effector, such as shaft assembly (164, 178, 186) and end effector (166, 180, 188) described above. Together, shrouds (7012, 7014) define a hollow interior (7015) which may, when suitably assembled, house suitable components of surgical instrument/tool (112, 117, 152, 154, 156) as would be apparent to one skilled in the art in view of the teachings herein. For example, proximal body (7010) may be configured to suitably house circuit boards, control units, batteries, ultrasonic transducer (162), toggle buttons (173, 174, 175, 195, 196, 197), trigger (183, 194), etc.

In the current example, shrouds (7012, 7014) include a plurality of aligned coupling sleeves (7036) that may receive friction fitting coupling bodies (7034). Complementary coupling sleeves (7036) of each shroud (7012, 7014) may receive a respective coupling body (7034) such that one coupling body (7034) is inserted into each complementary coupling sleeve (7036) of each shroud (7012, 7014). Coupling bodies (7034) may help inhibit shrouds (7012, 7014) from decoupling in the lateral direction (LD) by a frictional braking force generated between coupling body (7034) and respective coupling sleeves (7036). Coupling bodies (7034) and coupling sleeves (7036) may include any suitable geometry as would be apparent to one skilled in the art in view of the teachings herein. In one aspect of the disclosure, coupling bodies (7034) may contain a plurality of circumferentially extending ribs that may further promote engagement between the interior surfaces of coupling sleeves (7036) and coupling bodies (7034). Coupling bodies (7034) may be formed from any suitable material as would be apparent to one skilled in the art in view of the teachings herein.

Shrouds (7012, 7014) also include complementary support ribs (7038) lining a perimeter of the interior surface of shrouds (7012, 7014). Complementary support ribs (7038) of each shroud (7012, 7014) are configured to receive each other in a nested fashion in order to resist shrouds (7012, 7014) from vertically and longitudinally actuating relative to each other while coupled together. Therefore, ribs (7038) engage each other to inhibit shrouds (7012, 7014) from moving relative to each other in directions that are perpendicular to the to the lateral direction (LD) shown in FIG. 6.

Shrouds (7012, 7014) also include at least one latching assembly (7016). As will be described in greater detail below, while shrouds (7012, 7014) are suitably coupled to each other, latching assemblies (7016) are configured to move between a locked configuration and an unlocked configuration. While in the locked configuration, latching assemblies (7016) are configured to assist coupling bodies (7024) and sleeves (7036) in resisting shrouds (7012, 7014) from laterally decoupling. While in the unlocked configuration, latching assembly (7016) is configured to allow a user to at least initiate lateral separation of shrouds (7012, 7014) such that the user may overcome the frictional braking force inhibiting lateral separation of shrouds (7012, 7014).

Each latching assembly (7016) includes a resilient latch (7018) extending laterally from one shroud (7012), while the other shroud (7014) defines channel (7032) (see FIGS. 7A-7E) and an access hole (7030) in communication with each other. Resilient latch (7018) includes a resilient leg (7024) extending laterally away from its respective shroud (7012). As will be described in greater detail below, cam surface (7020) is configured to engage a corresponding cam surface (7026) of shroud (7014) as shrouds (7012, 7014) are laterally coupled together in order to drive resilient leg (7024) of latch (7018) from the relaxed position (see FIG. 7A) into the flexed position (see FIG. 7B). As will also be described in greater detail below, locking shoulder (7022) is configured to engage a corresponding locking shoulder (7028) defined by shroud (7014) when shrouds (7012, 7014) are laterally coupled together in order to inhibit shrouds (7012, 7014) from laterally decoupling.

Resilient leg (7024) terminates into a respective camming surface (7020) and locking shoulder (7022). Resilient leg (7024) is sufficiently flexible such that leg (7024) may deflect from a relaxed position (see FIG. 7A) into a flexed position (see FIG. 7B) in response to an external force. Additionally, resilient leg (7024) is sufficiently resilient such that leg (7024) may return to the relaxed position (see FIG. 7C) once the external force is sufficiently removed.

Figure 7A:
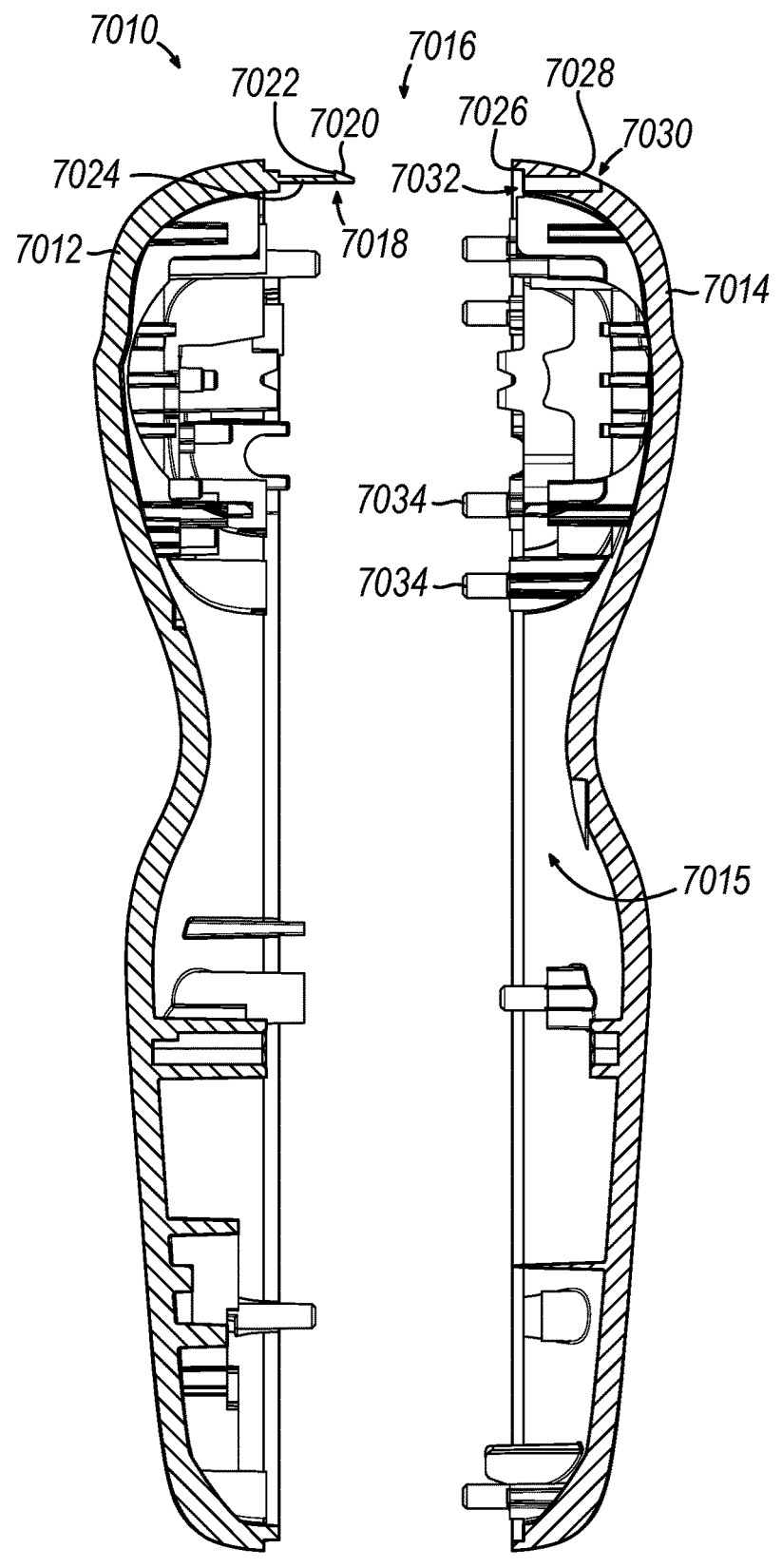
FIG. 7A depicts a sectional view of the proximal body of FIG. 6, where a first shroud and a second shroud are decoupled from each other.

FIGS. 7A-7E show an exemplary coupling and decoupling of shrouds (7012, 7014) utilizing latching assembly (7016). First, as shown in FIG. 7A, a user may align shrouds (7012, 7014) such that resilient latch (7018) is vertically and longitudinally aligned with channel (7032). It should be understood that while latch (7018) and channel (7032) are suitably aligned to couple shrouds (7012, 7014) together, complementary coupling sleeves (7036) of each shroud are suitably aligned, as well as complementary support ribs (7038) of each shroud (7012, 7014).

Figure 7B:
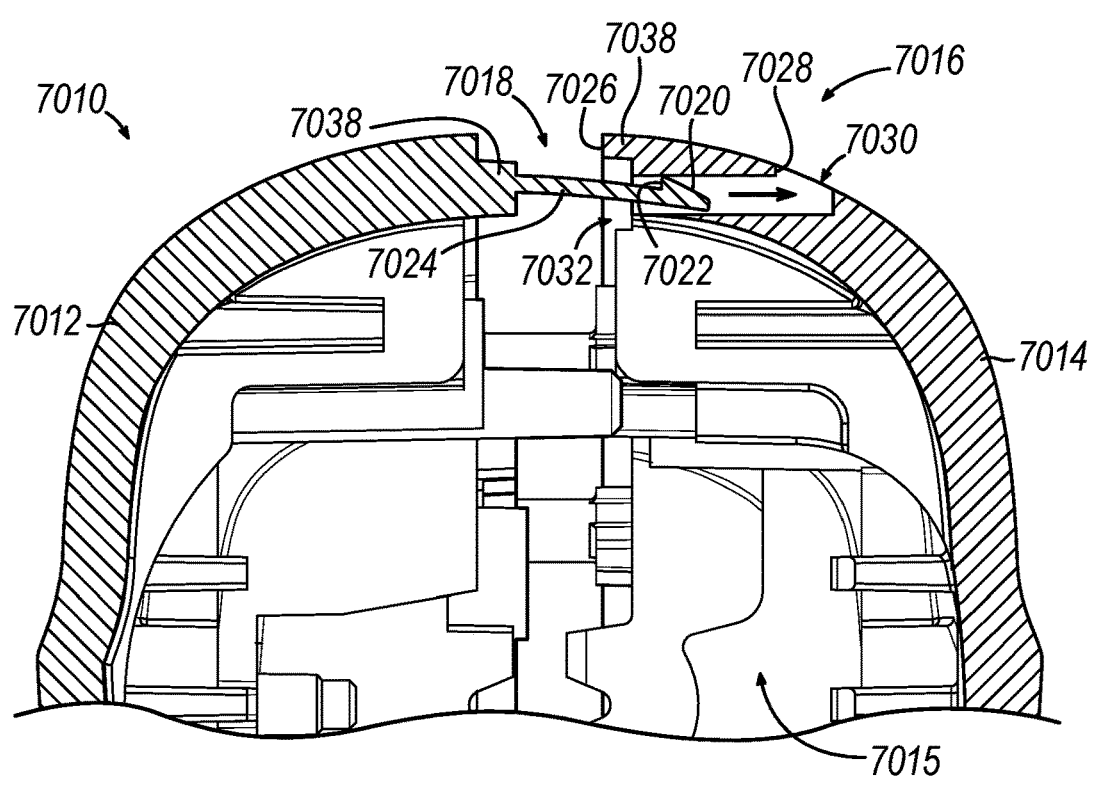
FIG. 7B depicts an enlarged sectional view of the proximal body of FIG. 6, where the first shroud and the second shroud of FIG. 7A actuated toward each other.

Next, as shown in FIG. 7B, with latch (7018) and channel (7032) aligned, a user may move shrouds (7012, 7014) toward each other such that contact between camming surfaces (7020, 7026) drives resilient leg (7024) from the relaxed position into a flexed position. As shrouds (7012, 7014) actuate further toward each other, camming surface (7020) of resilient latch (7018) may remain engaged with channel (7032) such that channel (7032) keeps latch (7018) in the flexed position.

Figure 7C:
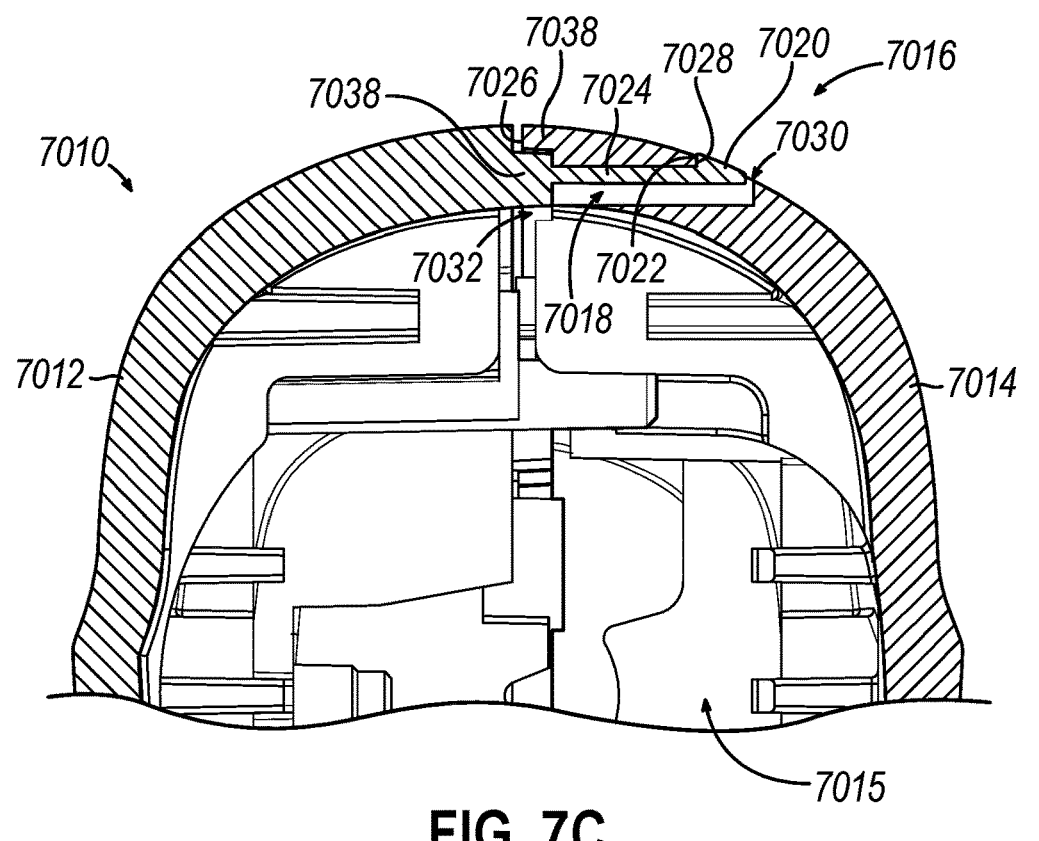
FIG. 7C depicts an enlarged sectional view of the proximal body of FIG. 6, where the first shroud and the second shroud of FIG. 7A are coupled together such that a latching assembly is in a locked configuration.

Next, as shown in FIG. 7C, once shrouds (7012, 7014) are fully coupled, camming surface (7020) is advanced laterally past the portion of channel (7032) forcing resilient latch (7018) into the flexed position such that resilient leg (7024) returns to the relaxed position and camming surface (7020) enters access hole (7030). With camming surface (7020) within access hole (7030), locking shoulder (7022) is directly adjacent to locking surface (7028), which defines a portion of access hole (7030). Locking shoulder (7022) and locking surface (7028) are directly adjacent to each other such that if shrouds (7012, 7014) attempt to laterally disengage each other, contact between shoulder (7022) and surface (7028) inhibits lateral movement of shrouds (7012, 7014) away from each other. Therefore, resilient latch (7018) is in the locked position while locking shoulder (7022) and locking surface (7028) are directly adjacent to each other, as shown in FIG. 7C. It should be understood that latching assembly (7016) also assists in aligning shrouds (7012, 7014) as shrouds (7012, 7014) are initially being coupled together, as well as keeping shrouds (7012, 7014) aligned during examplary use.

While in the locked position, a user may utilize proximal body (7010) in any suitable manner as would be apparent to one skilled in the art in view of the teachings herein. For example, a user may manipulate proximal body (7010) in order to suitably control surgical instrument/tool (112, 117, 152, 154, 156) in which proximal body (7010) is incorporated into. With latch (7018) in the locked position, latching assemblies (7016) enhance the structural robustness of proximal body (7010) by further inhibiting shrouds (7012, 7014) from inadvertently disassociating from each other.

Figure 7D:
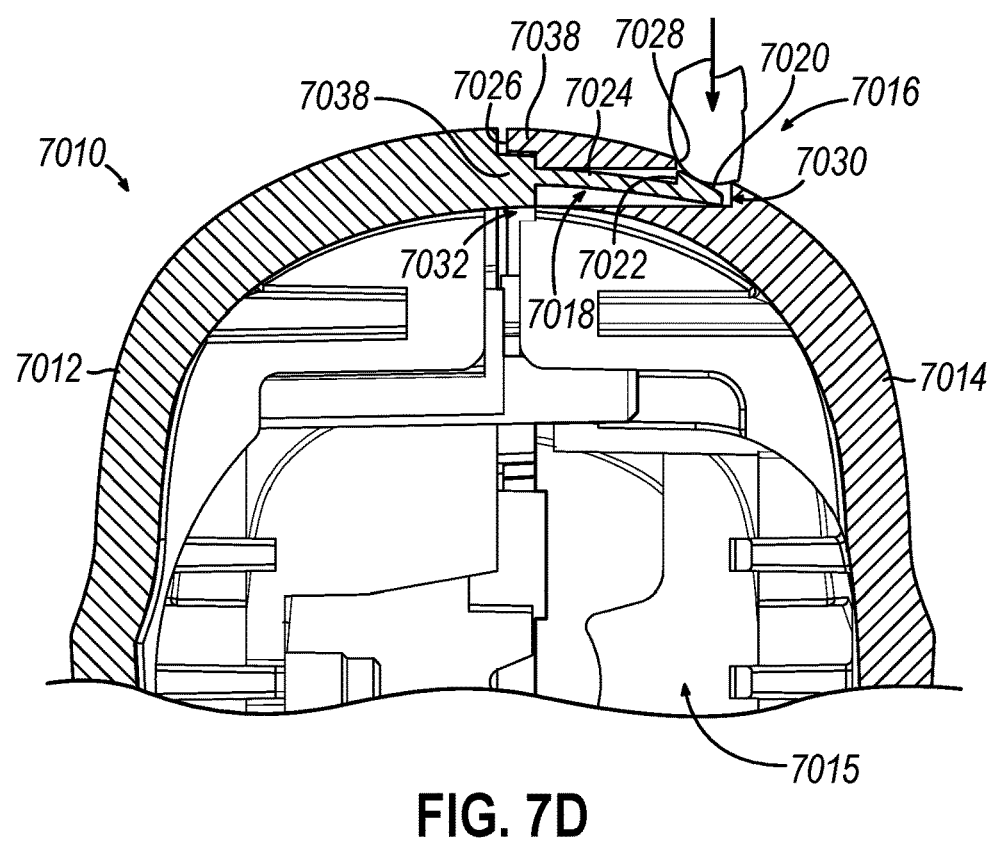
FIG. 7D depicts an enlarged sectional view of the proximal body of FIG. 6, where the first shroud and the second shroud of FIG. 7A are coupled together, where a user is actuating the latching assembly of FIG. 7C in an unlocked configuration.

After a user is finished utilizing proximal body (7010) in accordance with the description herein, it may be desirable to access various components housed within hollow interior (7015) for further processing (e.g., disposal, reuse, remanufacturing, etc.). If a user desires to access interior (7015) of proximal body (7010), the user may press down on terminating ends of resulting latch (7018) via access hole (7030) as shown in FIG. 7D. In particular, the user may press on resilient latch (7018) to flex resilient leg (7014) such that locking shoulder (7022) is no longer directly adjacent to locking surface (7028), thereby driving resilient latch (7018) into the unlocked configuration. With locking shoulder (7022) and locking surface (7028) separated from each other in the unlocked configuration, latching assembly (7016) may no longer inhibit lateral separation of shrouds (7012, 7014).

Figure 7E:
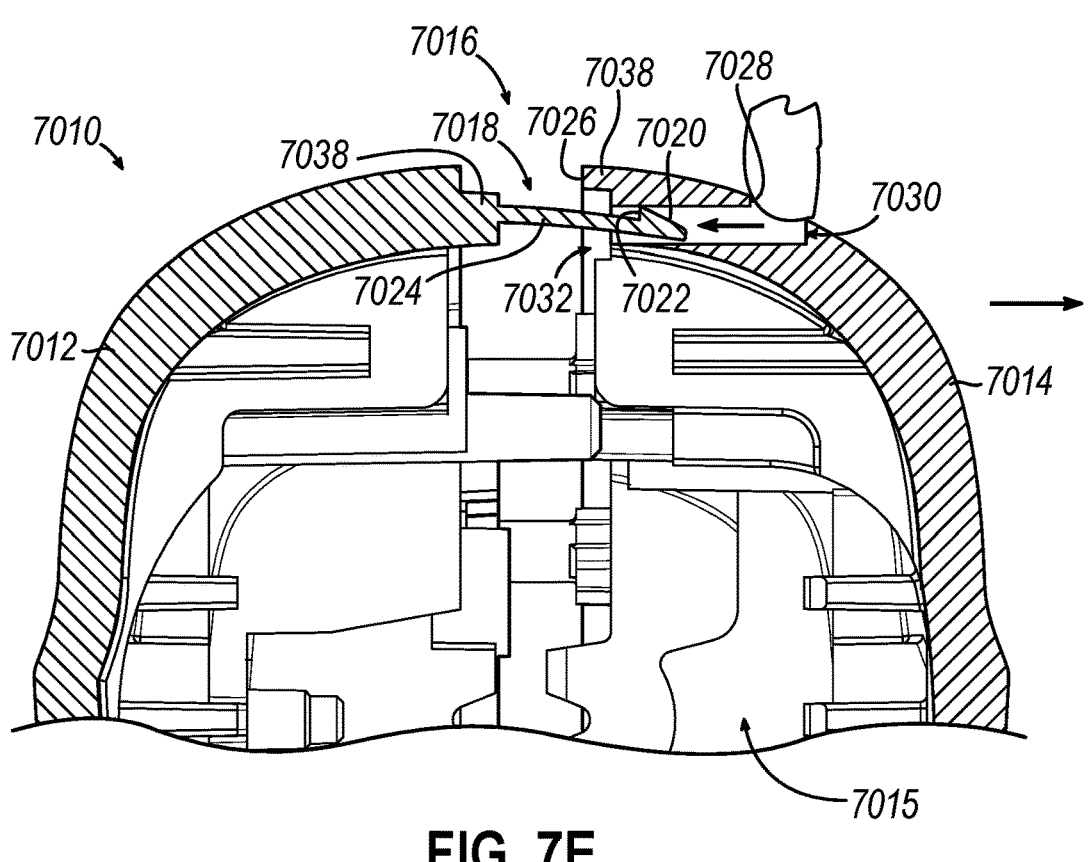
FIG. 7E depicts an enlarged sectional view of the proximal body of FIG. 6, where the first shroud and the second shroud of FIG. 7A are initially decoupled from each other.

Therefore, while a user presses downward on resilient latch (7018) via access hole (7030) as shown in FIG. 7D, the user may simultaneously pull the portions of shrouds (7012, 7014) directly adjacent to latching assembly (7016) apart from each other, as shown in FIG. 7E.

Once shrouds (7012, 7014) are suitably separated while latching assembly (7016) is in the unlocked configuration, camming surface (7020) of resilient latch (7018) reengages camming surface (7026) defined by channel (7032). Engagement between camming surfaces (7020, 7026) keeps resilient latch (7018) in the flexed position, thereby allowing a user to further pull shrouds (7012, 7014) apart. A user may further pull shrouds (7012, 7014) apart such that resilient latch (7018) exits channel (7032), thereby allowing latch (7018) to return to the relaxed position.

It should be understood that the resistance to lateral decoupling of shrouds (7012, 7014) provided by latching assembly (7016) may be controlled depending on whether latching assembly (7016) is in the locked configuration or the unlocked configuration. Therefore, if a user desires to decouple shrouds (7012, 7014) in accordance with the teachings herein, user may drive resilient latch (7018) into the flexed position such that locking shoulder (7022) and locking surface (7028) disassociate from each other. Otherwise, resilient latch (7018) will remain in the locked configuration, as shown in FIG. 7C, such that locking shoulder (7022) and locking surface (7028) inhibit inadvertent decoupling of shrouds (7012, 7014). In other words, latching assembly (7016) allows a user to easily decouple shrouds (7012, 7014) from one another; where shrouds (7012, 7014) remain structurally robust in the locked configuration, while shrouds (7012, 7014) are susceptible to separation in the unlocked configuration.

If shrouds (7012, 7014) of proximal body were strictly coupled together utilizing the frictional braking force provided by coupling bodies (7034) and coupling sleeves (7036), the lateral decoupling force required to pull shrouds (7012, 7014) apart may be substantially constant, regardless if the user desires to keep shrouds (7012, 7014) together, or separate shrouds (7012, 7014) to access internal components. In such instances, one may have to choose a frictional braking force structurally robust enough to keep shrouds (7012, 7014) together during exemplary use, but difficult to access internally; or choose a frictional braking force that allows easy decoupling of shrouds (7012, 7014), but also leaving shrouds (7012, 7014) susceptible to laterally decoupling during exemplary use.

While two latching assemblies (7016) are shown in the current example, any suitable number of latching assemblies (7016) may be utilized as would be apparent to one skilled in the art in view of the teachings herein. For example, a single latching assembly (7016) may be utilized. Additionally, while latching assemblies (7016) are shown positioned on the top of proximal body (7010); latching assemblies (7016) may be placed at any suitable location, or combination of locations, on proximal body (7010) as would be apparent to one skilled in the art in view of the teachings herein.

Figure 8:
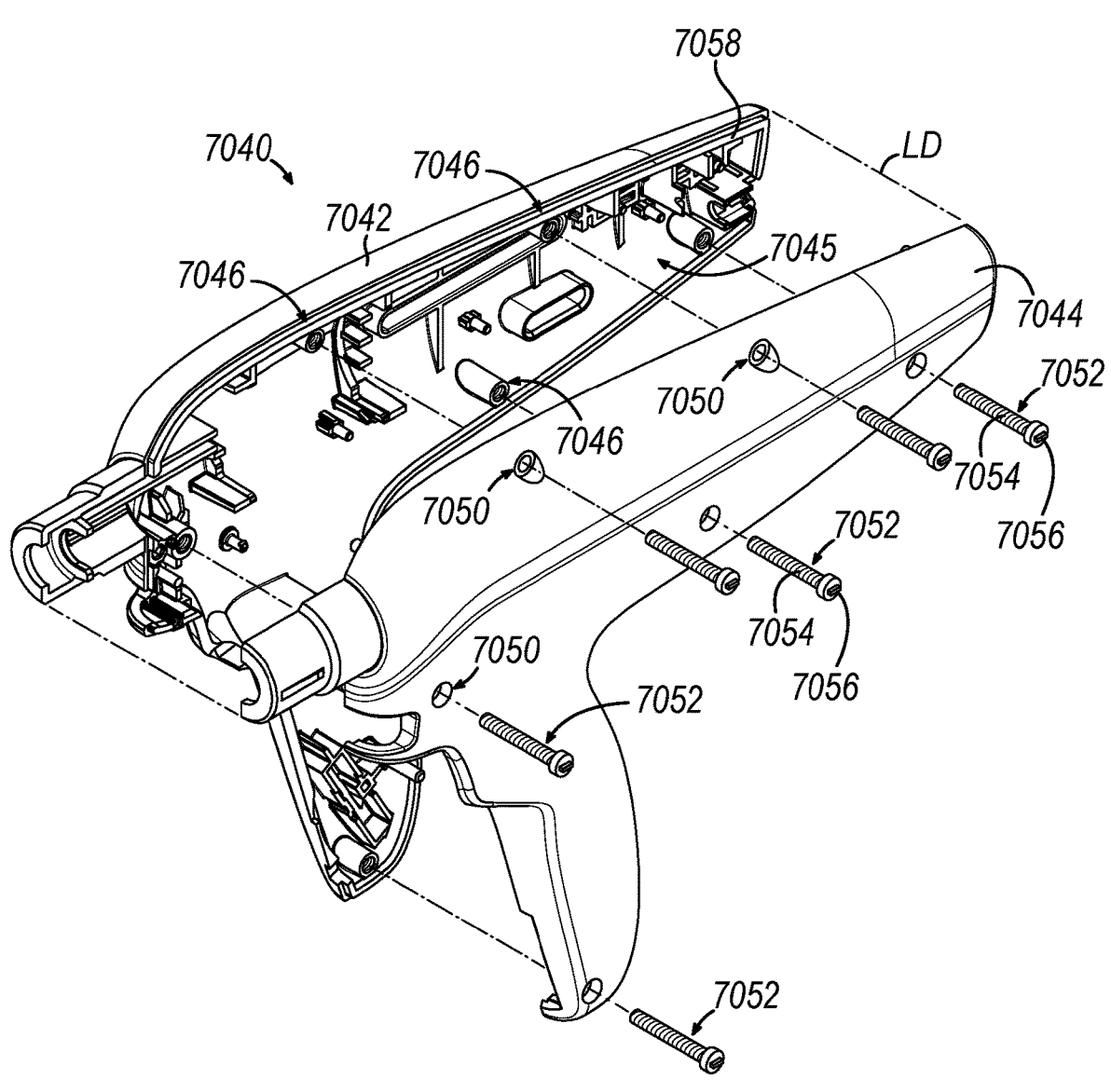
FIG. 8 depicts an exploded perspective view of another exemplary proximal body that may be readily incorporated into any of the surgical instruments shown herein.

While latching assembly (7016) is utilized to provide both structural robustness during exemplary use and internal access to harvest internal components after exemplary use, any other suitable structures may be utilized as would be apparent to one skilled in the art in view of the teachings herein. FIG. 8 shows another exemplary proximal body (7040) that may be readily incorporated into surgical instrument/tool (112, 117, 152, 154, 156). Proximal body (7040) includes a first shroud (7042) and a second shroud (7044)

that are configured to couple together in order to form proximal body (7040). As will be described in greater detail below, first shroud (7042) and second shroud (7044) contain complementary coupling features configured to resist inadvertent disassembly of proximal body (7040) during exemplary use, but also allow a user to separate shrouds (7042, 7044) after exemplary use in order to harvest internal components for processing.

In the current example, proximal body (7040) is shown as a handpiece, such that proximal body (7040) may be used in replacement of handpiece (160, 176, 185) described above. Proximal body (7040) is configured to suitably couple with a shaft assembly and end effector, such as shaft assembly (164, 178, 186) and end effector (166, 180, 188) described above. Together, shrouds (7042, 7044) define a hollow interior (7045) which may, when assembled, house suitable components of surgical instrument/tool (112, 117, 152, 154, 156) as would be apparent to one skilled in the art in view of the teachings herein. For example, proximal body (7040) may be configured to suitably house circuit boards, control units, batteries, ultrasonic transducer (162), toggle buttons (173, 174, 175, 195, 196, 197), trigger (183, 194), etc.

Similar to shrouds (7012, 7014) described above, shrouds (7042, 7044) also include complementary support ribs (7058) lining a perimeter of the interior surface of shrouds (7042, 7044). Complementary support ribs (7058) of each shroud (7042, 7044) are configured to receive each other in a nested fashion in order to resist shrouds (7042, 7044) from vertically and longitudinally actuating relative to each other while coupled together. Therefore, ribs (7058) engage each other to inhibit shrouds (7042, 7044) from moving relative to each other in directions that are perpendicular to the to the lateral direction (LD) shown in FIG. 8.

Rather than latching assemblies (7016), shroud (7042) includes a plurality of female threaded coupling sleeves (7046); while shroud (7044) defines a plurality of corresponding through holes (7050). Through holes (7050) and corresponding female threaded coupling sleeves (7046) are configured to receive a corresponding threaded twist screw (7052). Through holes (7050) are dimensioned large enough to receive threaded shafts (7054) of a corresponding twist screw (7052), but not large enough such that head (7056) of twist screw (7052) may travel past through holes (7050). Additionally, threaded shaft (7054) is configured to mesh with the threading of female threaded coupling sleeve (7046) such that rotation of threaded shaft (7054) relative to female threaded coupling sleeve (7046) longitudinally actuates threaded shaft (7054) relative the female threaded coupling sleeve (7046) and shroud (7042). Twist screws (7052) are dimensioned such that when suitably coupled, head (7056) abuts against a surface of shroud (7044), thereby compressing shrouds (7042, 7044) together; while the threaded engagement between threaded shaft (7054) and female threaded coupling sleeves (7046) inhibits twist screw (7052) from disassociating with shroud (7042). Therefore, a user may insert threaded shafts (70454) into a corresponding through hole (7050) until threaded shaft (7054) engages female threaded coupling sleeve (7046). Next, the user may then rotate twist screw (7052) with suitable torque at head (7056) until twist screw (7052) suitably couples shrouds (7042, 7044) together. Twist screws (7052) may therefore inhibit shrouds (7042, 7044) from disassociating with each other in the lateral direction (LD) during exemplary use.

After exemplary use, a user may remove threaded twist screws (7052) from shrouds (7042, 7044) in order to allow easy decoupling of shrouds (7042, 7044) in the lateral direction (LD) to harvest internal components for processing. A user may apply torque to head (7056) of each twist screw (7052) until threaded shaft (7054) decouples with female threaded coupling sleeve (7046). After all twist screws (7052) are decoupled from their respective female threaded coupling sleeve (7046), the user may laterally decouple shrouds (7042, 7044) to provide access to internal components. Therefore, twist screws (7052), female threaded coupling sleeves (7046), and through holes (7050) allow a user to easily decouple shrouds (7042, 7044) from one another; where shrouds (7042, 7044) remain structurally robust when twist screws (7052) are suitably assembled, while shrouds (7042, 7044) are susceptible to separation when twist screws (7052) suitably detached.

In some aspects of the disclosure, shrouds (7042, 7044) may include suitable through holes (7056) and coupling bodies (7034); along with use of female threaded coupling sleeves (7046), through holes (7050), and twist screws (7052). Any suitable combination of coupling bodies (7034) and twist screws (7052) may be utilized as would be apparent to one skilled in the art in view of the teachings herein.

Figure 9:
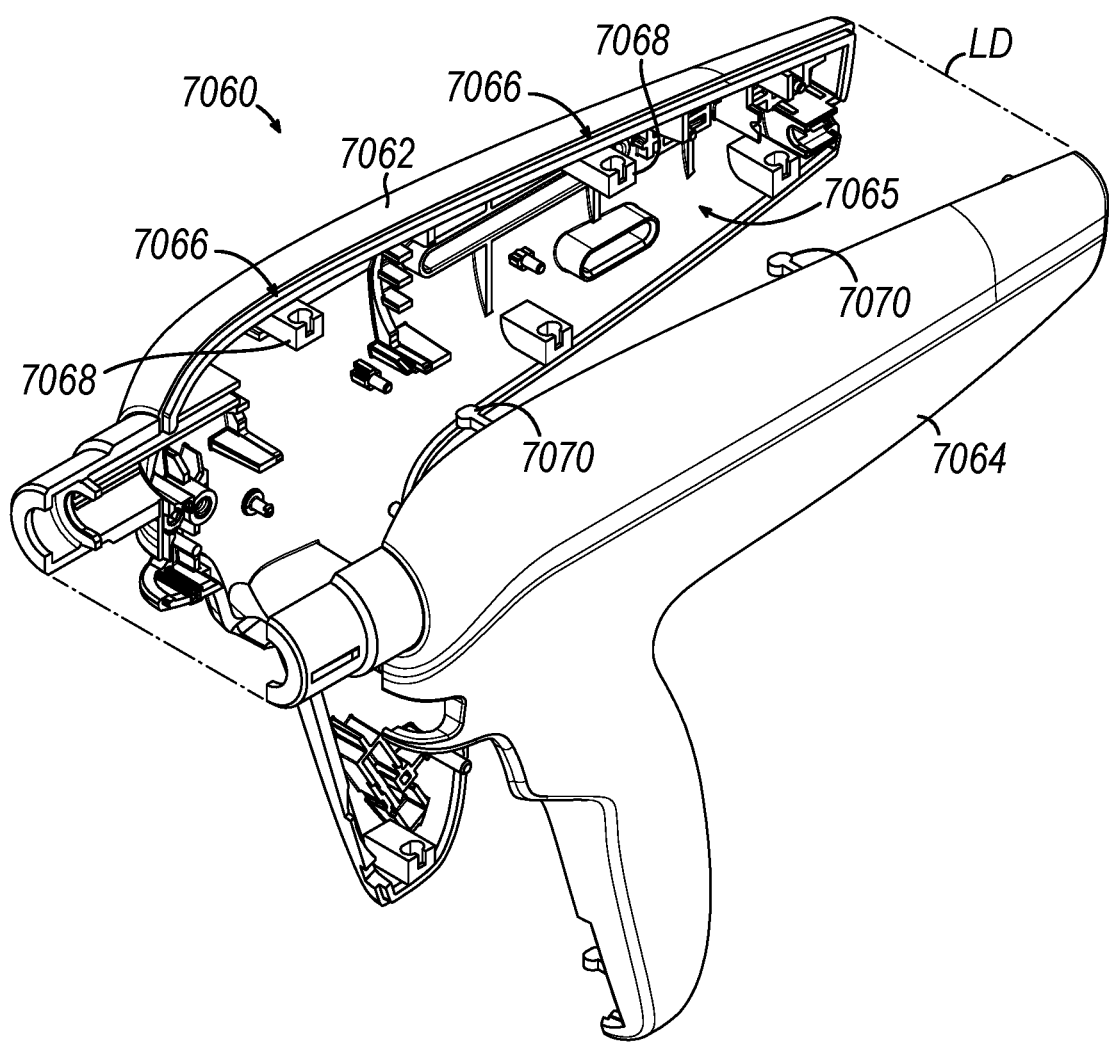
FIG. 9 depicts an exploded perspective view of another exemplary proximal body that may be readily incorporated into any of the surgical instruments shown herein.

FIG. 9 shows another exemplary proximal body (7060) that may be readily incorporated into surgical instrument/tool (112, 117, 152, 154, 156). Proximal body (7060) includes a first shroud (7062) and a second shroud (7064) that are configured to couple together in order to form proximal body (7060). As will be described in greater detail below, first shroud (7062) and second shroud (7064) contain complementary coupling features configured to resist inadvertent disassembly of proximal body (7060) during exemplary use, but also allow a user to separate shrouds (7062, 7064) after exemplary use in order to harvest internal components for processing.

In the current example, proximal body (7060) is shown as a handpiece, such that proximal body (7060) may be used in replacement of handpiece (160, 176, 185) described above. Proximal body (7060) is configured to suitably couple with a shaft assembly and end effector, such as shaft assembly (164, 178, 186) and end effector (166, 180, 188) described above. Together, shrouds (7062, 7064) define a hollow interior (7065) which may, when assembled, house suitable components of surgical instrument/tool (112, 117, 152, 154, 156) as would be apparent to one skilled in the art in view of the teachings herein. For example, proximal body (7060) may be configured to suitably house circuit boards, control units, batteries, ultrasonic transducer (162), toggle buttons (173, 174, 175, 195, 196, 197), trigger (183, 194), etc.

Rather than having latching assembly (7016) or twist screws (7052), shrouds (7062, 7064) contain vertical direction coupling assemblies (7066). Vertical direction coupling assemblies (7066) are configured to allow shrouds (7062, 7064) to actuate vertically relative to each other in order to suitably couple and decouple. Vertical direction coupling assembly (7066) includes a plurality of first coupling bodies (7068) extending from first shroud (7062) and a plurality of corresponding second coupling bodies (7070) extending from second shroud (7064) toward first shroud (7062).

Figure 10A:
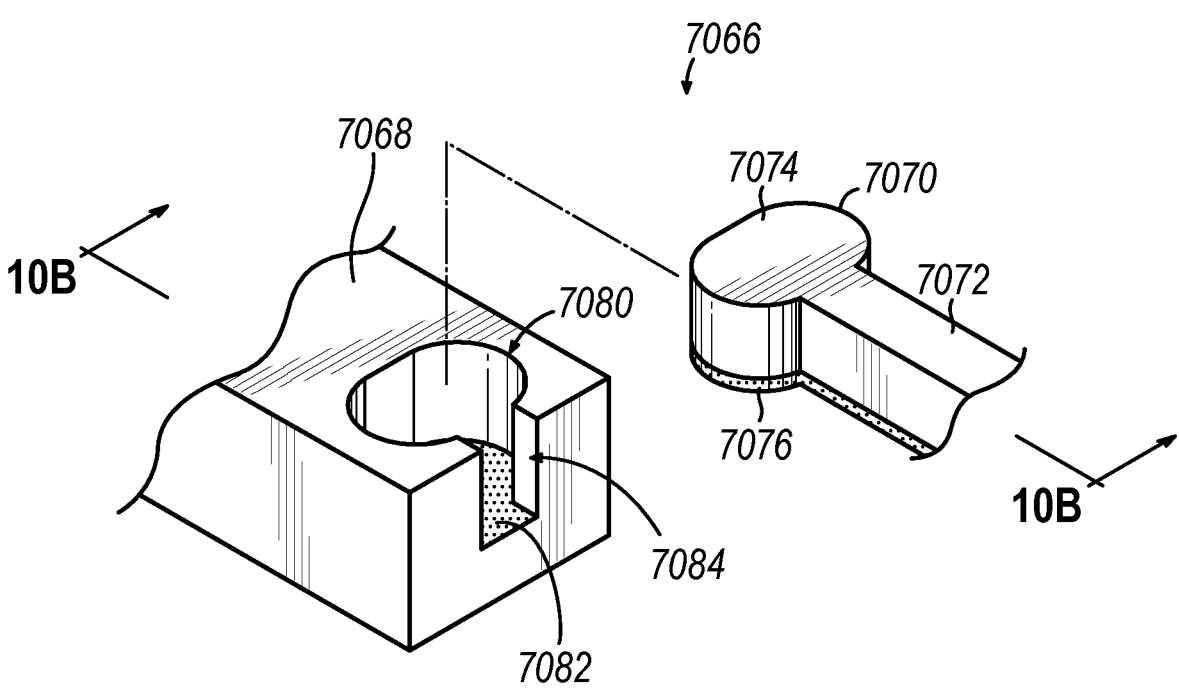
FIG. 10A depicts an enlarged perspective view of a coupling assembly of the proximal body of FIG. 9 in a decoupled configuration.

As best shown in FIG. 10A, first coupling body (7068) defines a complementary channel (7080) extending from a top surface of first coupling body (7068) and terminating into a magnetic floor (7082). First coupling body (7068) also defines a slot (7084) in communication with channel (7080) such that slot (7084) and channel (7080) are dimensioned to receive a corresponding second coupling body (7070).

Figure 10B:
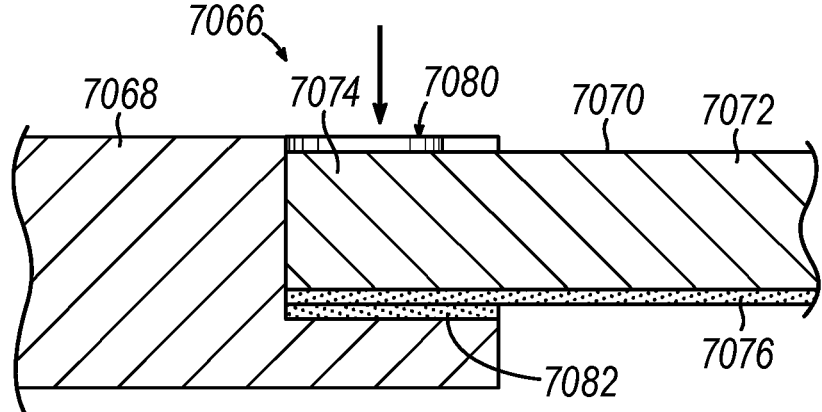
FIG. 10B depicts an enlarged cross-sectional view of the coupling assembly taken along section line 10B-10B of FIG. 10A in a coupled configuration.

Second coupling body (7070) includes a narrow portion (7072) terminating into a widened portion (7074). Second coupling body (7070) also includes a magnetic surface (7076) configured to be directly adjacent and/or in contract with magnetic floor (7082) of first coupling body (7068). Narrow portion (7072) extends away from sheath (7064) and is dimensioned to suitably fit within slot (7084) defined by first coupling body (7068). Widened portion (7074) is dimensioned to fit within complementary channel (7080) defined by first coupling body (7068). When suitably coupled as shown in FIG. 10B, the complementary geometries of slot (7084) and channel (7080) respectively with narrow portion (7072) and widened portion (7074) are configured to inhibit relative movement between shrouds (7062, 7064) while suitably coupled in every direction except the vertical direction. Additionally, magnetic surface (7076) and magnetic floor (7082) are magnetically attracted toward each other, such that while first and second coupling bodies (7068, 7070) are coupled to each other, the magnetic attraction between surface (7076) and floor (7082) inhibits second coupling body (7070) from actuating vertically out of the confines of first coupling body (7068); thereby inhibiting relative movement between shrouds (7062, 7064) in the vertical direction as well.

It should be understood that the magnetic attraction between floor (7082) and surface (7076) is suitably strong enough such that sheaths (7062, 7064) do not inadvertently disassociate from each other during exemplary use in accordance with the description herein. However, the magnetic attraction between floor (7082) and surface (7076) may be overcome with a sufficient amount of force in the vertical direction when a user desires to intentionally decouple sheaths (7072, 7064) from each other to access hollow interior (7065) in order to harvest internal components for processing. In other words, shrouds (7062, 7064) remain structurally robust during exemplary use, while shrouds (7062, 7064) are susceptible to separation in response to a sufficient force in the vertical direction via coupling assembly (7066), which allows a user to easily decouple shrouds (7062, 7064) from one another. It should be understood that, in the vertical direction, coupling assemblies (7066) also assist in aligning shrouds (7062, 7064) as shrouds (7062, 7064) are initially being coupled together, as well as keeping shrouds (7062, 7064) aligned during example use.

Figure 11A:
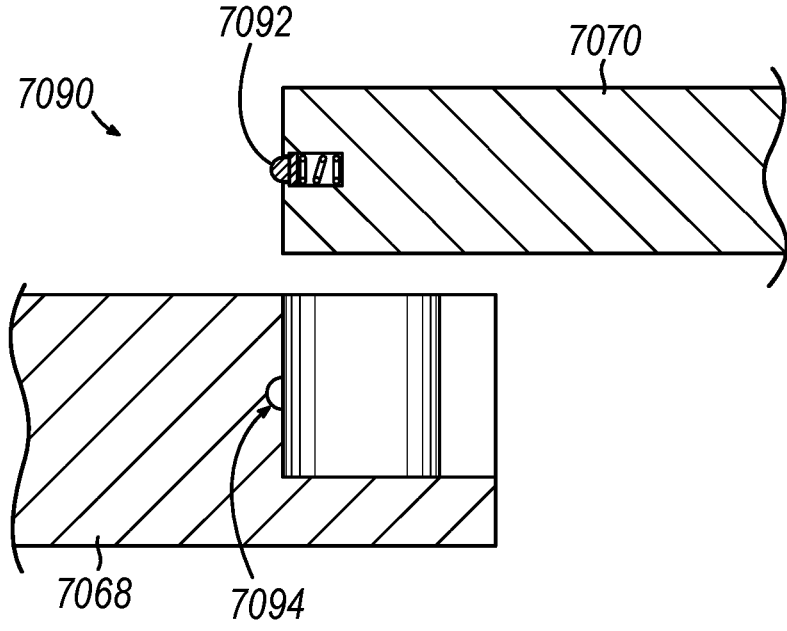
FIG. 11A depicts an enlarged sectional view of an alternative coupling assembly in a decoupled configuration.
Figure 11B:
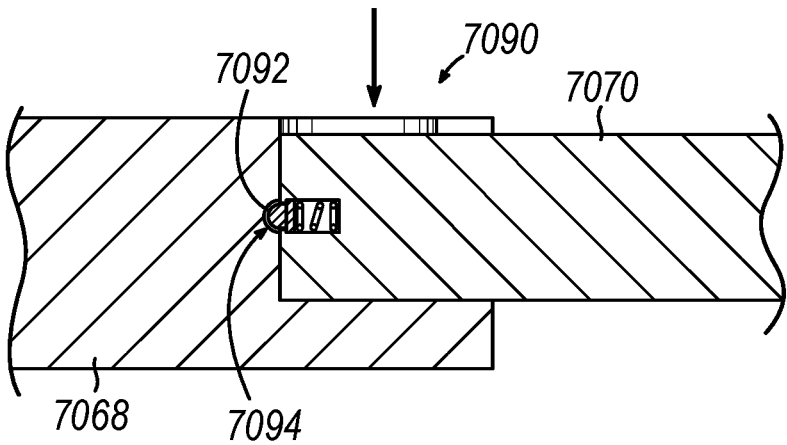
FIG. 11B depicts an enlarged sectional view of the coupling assembly of FIG. 11A in a coupled configuration.

While magnetic attraction is used in the current example to inhibit relative movement between shrouds (7062, 7064) in the vertical direction, any other suitable structures may be utilized to inhibit relative vertical movement as would be apparent to one skilled in the art in view of the teachings herein. FIGS. 11A-11B show an alternative coupling assembly (7090) that may be readily incorporated into shroud (7062, 7064) in replacement of coupling assembly (7066) described above. Therefore, coupling assembly (7090) is substantially similar to coupling assembly (7066) described above, with differences elaborated below.

In particular, rather than magnets, coupling assembly (7090) includes a resilient nub (7092) associated with an exterior surface of second body (7070); while coupling assembly (7090) also includes a corresponding recess (7094) defined by an interior surface of first coupling body (7068). Resilient nub (7092) and recess (7094) are dimensioned to interact with each other in a snap-fit fashion such that while coupled together, a frictional braking force between resilient nub (7092) and recess (7094) inhibits relative movement between first body (7068) and second body (7070). However, the frictional braking force between resilient nub (7092) and recess (7094) may be overcome with a sufficient amount of force in the vertical direction when a user desires to intentionally decouple sheaths (7072, 7064) from each other to access hollow interior (7065) in order to harvest internal components for processing. In other words, coupling assembly (7090) allows a user to easily decouple shrouds (7062, 7064) from one another; where shrouds (7062, 7064) remain structurally robust during exemplary use, while shrouds (7062, 7064) are susceptible to separation in response to a sufficient force in a the vertical direction.

FIG. 12 shows another exemplary proximal body (7100) that may be readily incorporated into surgical instrument/tool (112, 117, 152, 154, 156). Proximal body (7100) includes a first shroud (7102) and a second shroud (7104) that are configured to couple together in order to form proximal body (7100). As will be described in greater detail below, first shroud (7102) and second shroud (7104) contain complementary coupling features configured to resist inadvertent disassembly of proximal body (7100) during exemplary use, but also allow a user to separate shrouds (7102, 7104) after exemplary use in order to harvest internal components for processing.

In the current example, proximal body (7100) is shown as a handpiece, such that proximal body (7100) may be used in replacement of handpiece (160, 176, 185) described above. Proximal body (7100) is configured to suitably couple with a shaft assembly and end effector, such as shaft assembly (164, 178, 186) and end effector (166, 180, 188) described above. Together, shrouds (7102, 7104) define a hollow interior (7105) which may, when assembled, house suitable components of surgical instrument/tool (112, 117, 152, 154, 156) as would be apparent to one skilled in the art in view of the teachings herein. For example, proximal body (7100) may be configured to suitably house circuit boards, control units, batteries, ultrasonic transducer (162), toggle buttons (173, 174, 175, 195, 196, 197), trigger (183, 194), etc.

Each shroud (7102, 7104) in the current embodiment includes a respective complementary support rib (7106, 7108), which may be substantially similar to complementary support ribs (7038) described above. Each complementary support rib (7106, 7108) lines a perimeter of the interior surface of respective shrouds (7102, 7104) and extend away from a respective recessed surface (7110, 7112). Shrouds (7102, 7104) are configured to couple together via lateral movement relative to each other. During coupling, as shown in FIGS. 13A-13B, complementary support ribs (7106, 7108) of each shroud (7102, 7104) are configured to receive each other in a nested fashion such that support rib (7106) abuts against recessed surface (7112), and such that support rib (7108) abuts against recessed surface (7110). The nested engagement between support ribs (7106, 7108), while shrouds (7102, 7104) are suitably coupled, inhibits shrouds (7102, 7104) from vertically and longitudinally actuating relative to each other while coupled together. Therefore, ribs (7106, 7108) engage each other to inhibit shrouds (7102, 7104) from moving relative to each other in directions that are perpendicular to the lateral direction (LD).

Shrouds (7102, 7104) also include a respective magnet (7114, 7116) located on surface (7110) and support rib (7108) of respective shrouds (7102, 7104). While in the current aspect of the disclosure, magnets (7114, 7116) are shown on surface (7110) and support rib (7108), this is merely optional, as magnets (7114, 7116) may be located on any suitable components of shrouds (7102, 7104) as would be apparent to one skilled in the art in view of the teachings herein. Magnets (7114, 7116) are magnetically attracted toward each other, such that while support ribs (7106, 7108) are nested with each other, the magnetic attraction between magnets (7114, 7116) inhibits support ribs (7106, 7108) from actuating laterally out of engagement with each other;

thereby inhibiting relative movement between shrouds (7102, 7104) in the lateral direction as well.

It should be understood that the magnetic attraction between magnets (7114, 7116) is suitably strong enough such that sheaths (7102, 7104) do not inadvertently disassociate from each other during exemplary use in accordance with the description herein. However, the magnetic attraction between magnets (7114, 7116) may be overcome with a sufficient amount of force in the lateral direction when a user desires to intentionally decouple sheaths (7102, 7104) from each other to access the hollow interior (7105) in order to harvest internal components for processing. In other words, magnets (7114, 7116) allows a user to easily decouple shrouds (7102, 7104) from one another; where shrouds (7102, 7104) remain structurally robust during exemplary use, while shrouds (7102, 7104) are susceptible to separation in response to a sufficient force in the vertical direction.

Figure 14A:
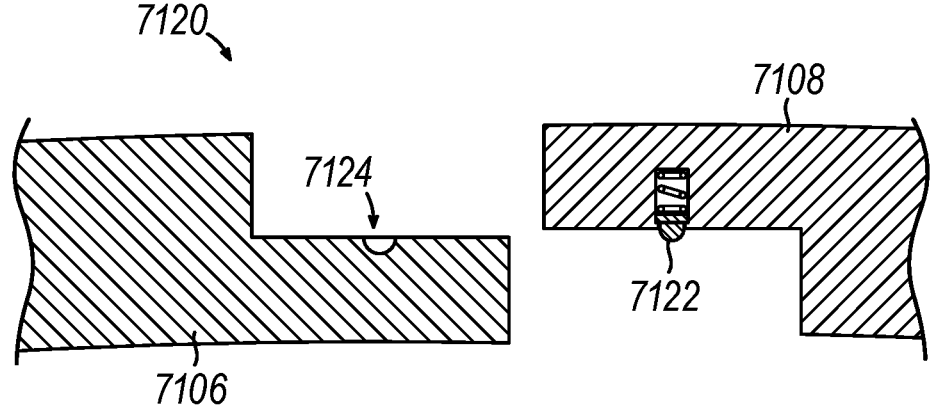
FIG. 14A depicts an enlarged sectional view of an alternative coupling assembly in a decoupled configuration.
Figure 14B:
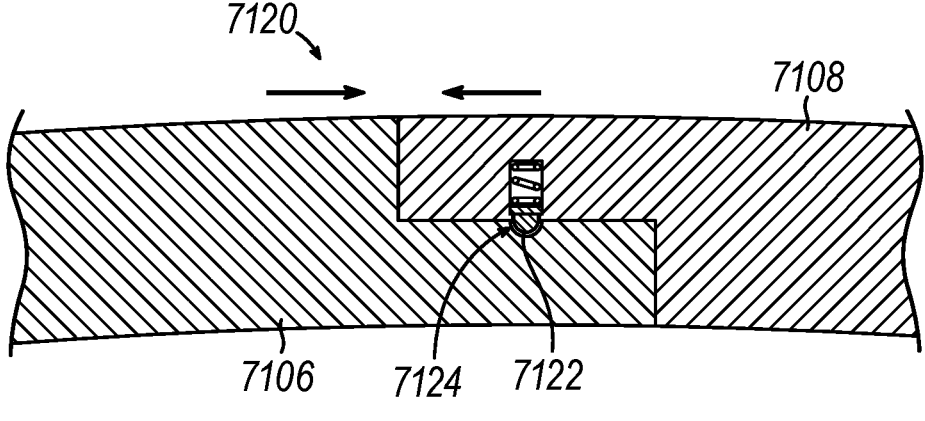
FIG. 14B depicts an enlarged sectional view of the coupling assembly of FIG. 14A in a coupled configuration.

While magnetic attraction is used in the current example to inhibit relative movement between shrouds (7102, 7104) in the lateral direction, any other suitable structures may be utilized to inhibit relative vertical movement as would be apparent to one skilled in the art in view of the teachings herein. FIGS. 14A-14B show an alternative coupling assembly (7120) that may be readily incorporated into shroud (7102, 7104) in replacement of magnets (7114, 7116) described above.

Rather than magnets, coupling assembly (7120) includes a resilient nub (7122) associated with an exterior surface of support rib (7108); while coupling assembly (7120) also includes a corresponding recess (7124) defined by a complementary surface of support rib (7106). Resilient nub (7122) and recess (7124) are dimensioned to interact with each other in a snap-fit fashion such that while coupled together, a frictional braking force between resilient nub (7122) and recess (7124) inhibits relative movement between support ribs (7106, 7108). However, the frictional braking force between resilient nub (7122) and recess (7124) may be overcome with a sufficient amount of force in the lateral direction when a user desires to intentionally decouple sheaths (7102, 7104) from each other to access the hollow interior (7105) in order to harvest internal components for processing. In other words, coupling assembly (7120) allows a user to easily decouple shrouds (7102, 7104) from one another; where shrouds (7102, 7104) remain structurally robust during exemplary use, while shrouds (7102, 7104) are susceptible to separation in response to a sufficient force in the lateral direction.

In some instances, where proximal body (7010, 7040, 7060, 7100) is intended to be processed for reuse or remanufacturing, it may be desirable to prevent re-assembly of shrouds (7012, 7014, 7042, 7044, 7062, 7064, 7102, 7104) with each other or with other suitable components of surgical instrument/tool (112, 117, 152, 154, 156) coupled to proximal body (7010, 7040, 7060, 7100) if critical parts forming surgical instrument/tool (112, 117, 152, 154, 156) are out of shape or out of a specified tolerance. For example, one or more features of shrouds (7012, 7014, 7042, 7044, 7062, 7064, 7102, 7104) or other suitable components could be used as a blocking means to prevent re-assembly if such features become distorted or damaged outside a tolerance range that is acceptable. As one example, a clamp trigger, similar to trigger (183) described above, may be coupled to proximal body (7010) via coupling body (7034) and couplings sleeves (7036). During exemplary use, forces acting on trigger (183) during pivotal movement of trigger (183) may result in damage to coupling sleeves (7036) and or trigger (183), which would then prevent reassembly once sheaths (7012, 7014) are suitably processed for reuse (e.g., sterilized).

As mentioned above, in some instances after exemplary use of proximal body (7010, 7040, 7060, 7100), shrouds (7012, 7014, 7042, 7044, 7062, 7064, 7102, 7104) may be processed for reuse and or remanufacturing. As also mentioned above, hollow interior (7015, 7045, 7065, 7105) may house suitable components of surgical instrument/tool (112, 117, 152, 154, 156) as would be apparent to one skilled in the art in view of the teachings herein, such as circuit board and control units. Therefore, in instances where electrical components are contained within hollow interior (7015, 7045, 7065, 7105), it may be desirable to ensure such electrical components are suitably removed from shrouds (7012, 7014, 7042, 7044, 7062, 7064, 7102, 7104) before shrouds (7012, 7014, 7042, 7044, 7062, 7064, 7102, 7104) are processed for reuse and/or remanufacturing. Ensuring electrical components are suitably removed before shrouds (7012, 7014, 7042, 7044, 7062, 7064, 7102, 7104) are processed may prevent such electrical components from being inadvertently exposed to substances used during processing that may damage electrical components and/or render them unsuitable for further use.

Figure 15B:
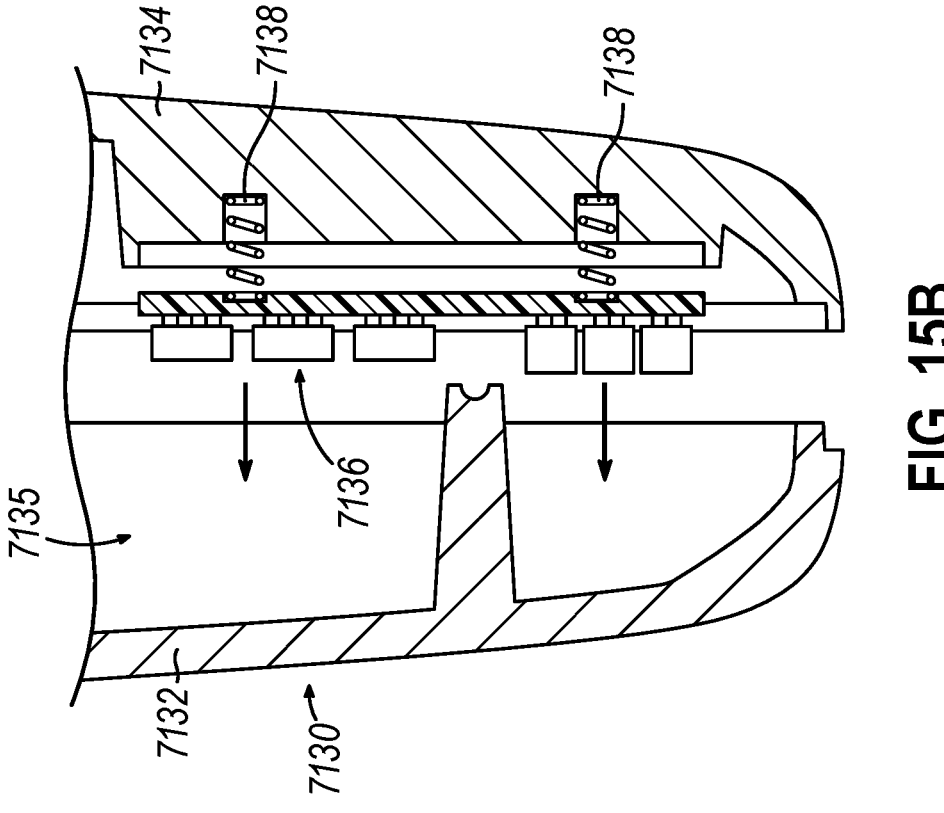
FIG. 15B depicts an enlarged sectional view of the proximal body of FIG. 15A, wherein the proximal body is disassembled with the electrical component biased away from a shroud of the proximal body.
Figure 15A:
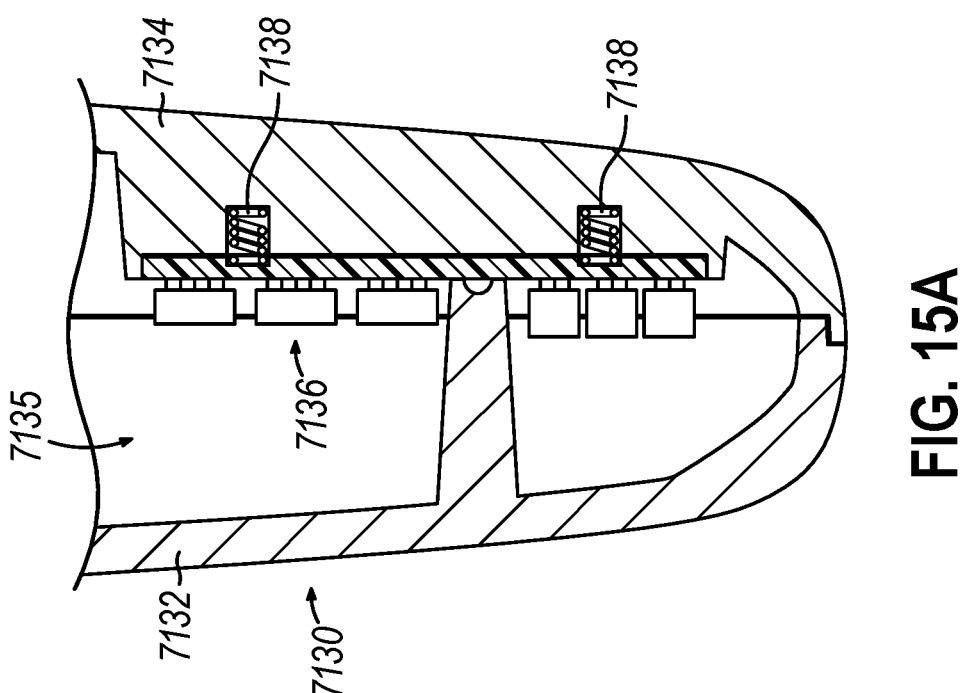
FIG. 15A depicts an enlarged sectional view of another exemplary proximal body that may be readily incorporated into any of the surgical instruments shown herein, where the proximal body is assembled with an electrical component housed therein.

FIGS. 15A-15B show an exemplary proximal body (7130) that may be substantially similar to proximal body (7010, 7040, 7060, 7100) described above, with differences elaborated below. Therefore, proximal body (7130) includes a first shroud (7132) and a second shroud (7134) which may be substantially similar to shrouds (7012, 7014, 7042, 7044, 7062, 7064, 7102, 7104) described above, with differences elaborated below. Together, shrouds (7132, 7134) define a hollow interior (7135). Shroud (7134) includes biasing springs (7138) that are interposed between an interior surface of shroud (7134) and a suitable electrical component (7136). When shrouds (7132, 7134) are assembled, as shown in FIG. 15A, biasing springs (7138) bias electrical component (7136) against first shroud (7132), or any other suitable structure, thereby forcing electrical component (7136) into a suitable position within hollow interior (7135).

After exemplary use, shrouds (7132, 7134) may be disassembled for processing in accordance with the teachings herein. During disassembly, proximal body (7130) may be disassembled to remove electrical component (7136) from shroud (7134) such that electrical component (7136) does not inadvertently get processed with shroud (7134). As shown in FIG. 15B, once shrouds (7132, 7134) are disassembled, biasing springs (7138) drive electrical component (7136) away from shroud (7134) such that electrical component (7136) is prominently presented to the user disassembling proximal body (7130). Therefore, biasing springs (7138) help drive electrical component (7136) into an exposed position such that a person disassembling proximal body (7130) may be reminded to further remove electrical component (7136).

Figure 16A:
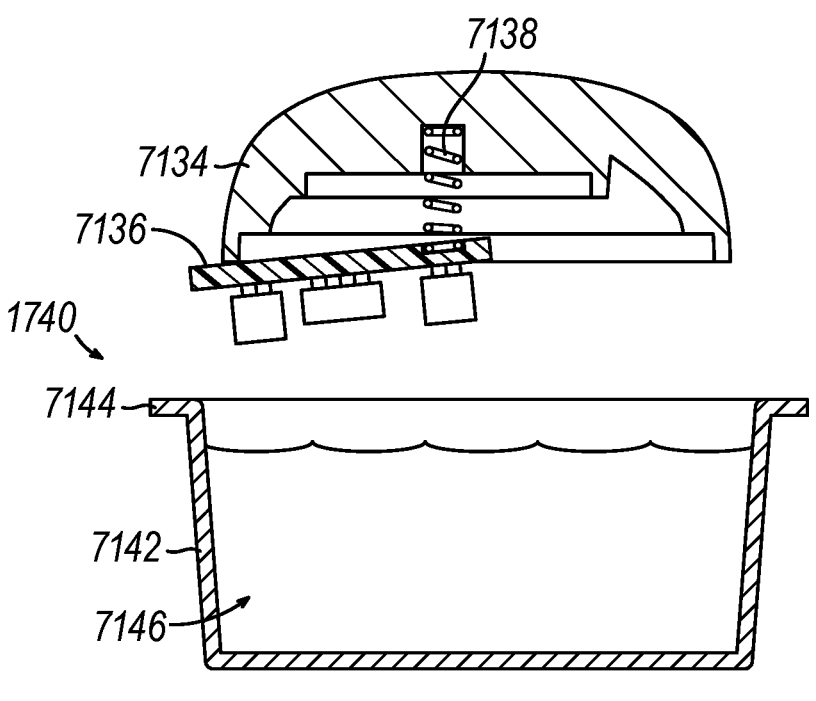
FIG. 16A depicts a sectional view of a shroud of the proximal body of FIG. 15A still coupled with the electrical component in FIG. 15A placed above an exemplary dip tray.
Figure 16B:
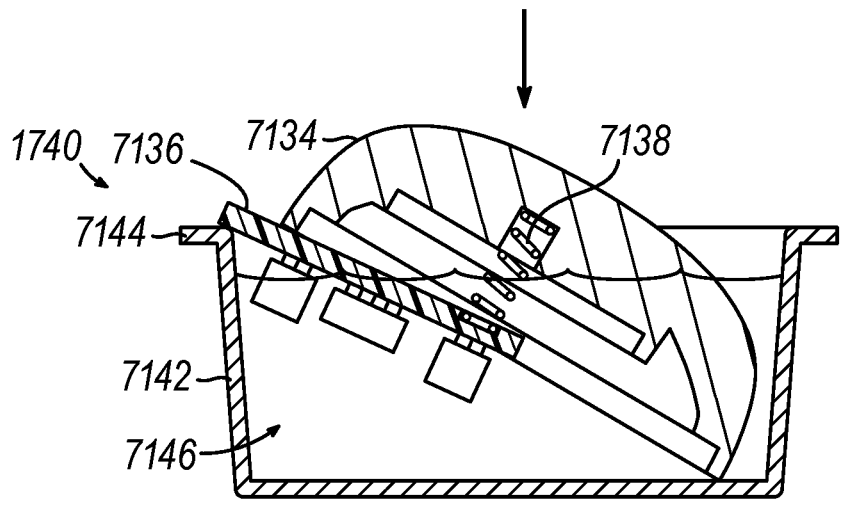
FIG. 16B depicts a sectional view of the shroud of FIG. 16A coupled with the electrical component of FIG. 15A inappropriately placed within the dip tray of FIG. 16A.
Figure 17A:
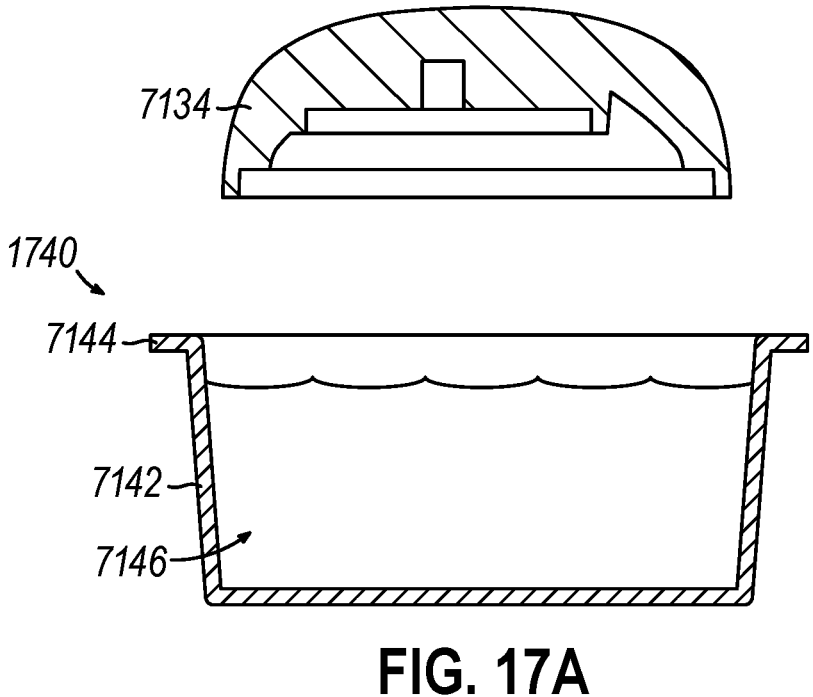
FIG. 17A depicts a sectional view of the shroud of FIG. 16A decoupled from the electrical component of FIG. 15A and placed above the dip tray of FIG. 16A.
Figure 17B:
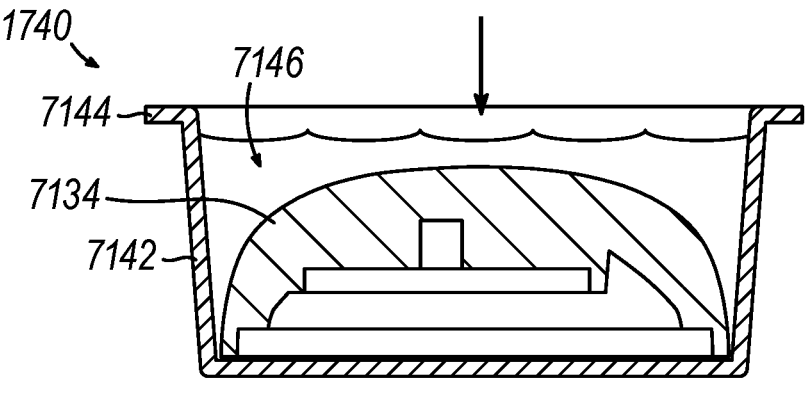
FIG. 17B depicts a sectional view of the shroud of FIG. 16A decoupled from the electrical component of FIG. 15A and appropriately placed within the dip tray of FIG. 16A.

In some instances, it may be desirable to inhibit a user who is processing shroud (7132, 7134) for reuse and/remanufacturing from inadvertently dipping electrical component (7136) into a dip tray during processing. FIGS. 16A-17B show an exemplary dip tray (7140) that may be used to process shroud (7132, 7134) by exposing a used shroud (7132, 7134) in a suitable cleaning fluid to clean shroud (7132, 7134). Dip tray (7140) includes a body (7142) defining a reservoir (7146) that may house a suitable cleaning fluid. Dip tray (7140) also includes a perimeter (7144) that defines an opening dimensioned to receive shroud (7134) for processing. As shown in FIGS. 16A-16B, perimeter (7144) is dimensioned with a specific geometry that may inhibit suitably receiving shroud (7134) within reservoir (7146) if electrical component (7136) is not removed from shroud (7134). As shown in FIGS. 17A-17B, perimeter (7144) is also dimensioned with a specific geometry that suitably receives shroud (7134) within reservoir (7146) if electrical component (7136) is removed from shroud (7134). Therefore, if a user inadvertently keeps electrical component (7136) attached to shroud (7134), user may be reminded to removed electrical component (7136) when attempting to insert shroud (7134) within dip tray (7140), as shroud (7143) will not suitably fit within dip tray (7140).

Figure 18A:
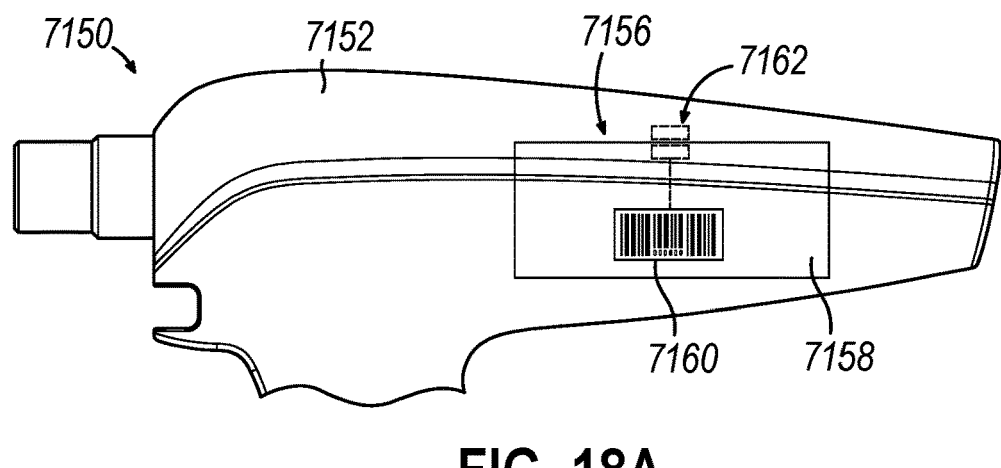
FIG. 18A depicts an enlarged elevational side view of another exemplary proximal body that may be readily incorporated into any of the surgical instruments shown herein.
Figure 18B:
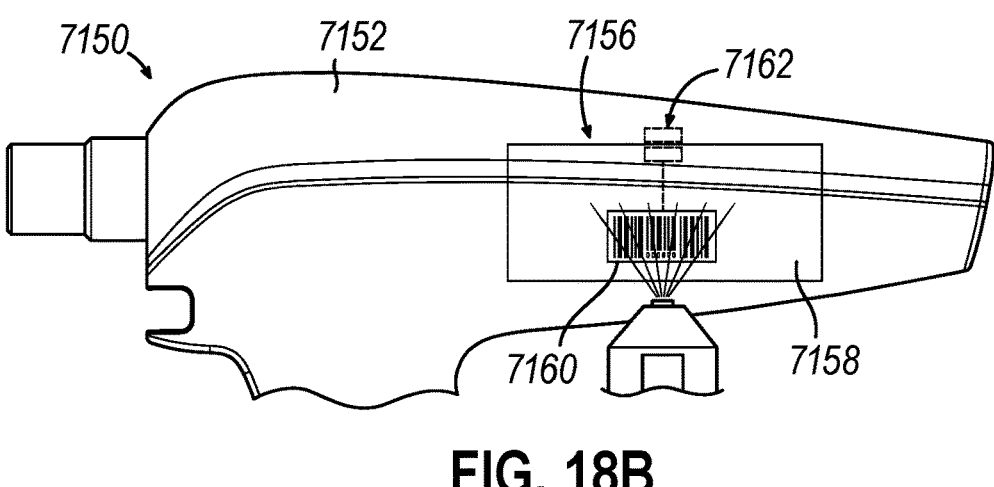
FIG. 18B depicts an enlarged elevational side view of the proximal body of FIG. 18A, where a scanning device is scanning a bar code of the proximal body.
Figure 18C:
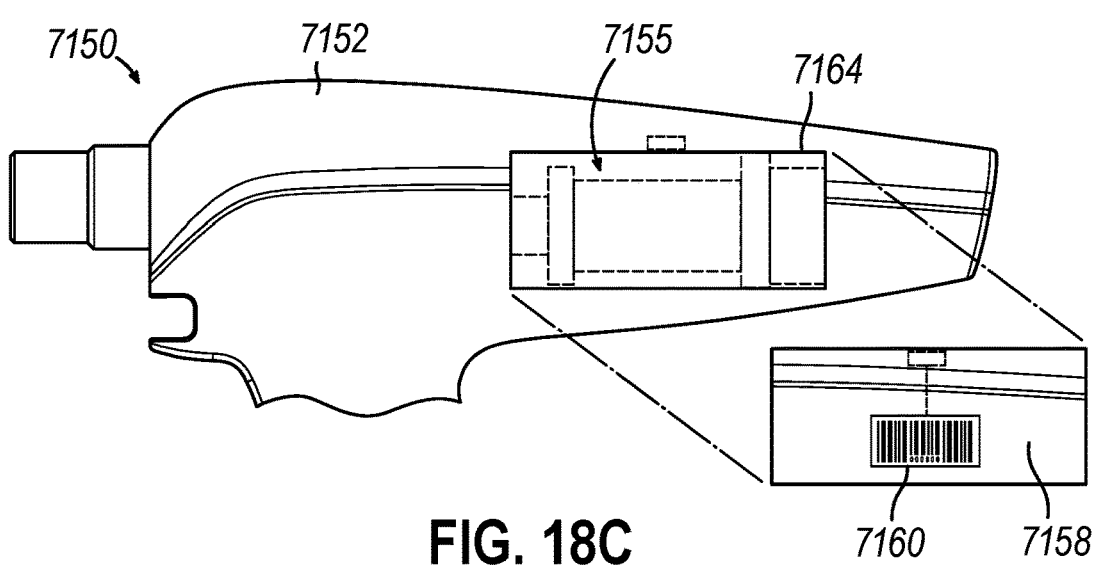
FIG. 18C depicts an enlarged elevational side view of the proximal body of FIG. 18A, where a hatch door of the proximal body is removed.

FIGS. 18A-18C show another exemplary proximal body (7150) that may be substantially similar to proximal body (7010, 7040, 7060, 7100, 7130) described above, with differences elaborated below. Therefore, proximal body (7150) includes sheath (7152) that may define a hollow interior (7155). Sheath (7152) includes a hatch assembly (7156) configured to provide suitable access to hollow interior (7155) in accordance with the description herein.

Hatch assembly (7156) includes a hatch door (7158) removably coupled to an opening (7164) defined by sheath (7152), a bar code (7160), and an electric latch assembly (7162). Latch assembly (7162) is configured to lock hatch door (7158) such that hatch door (7158) is inhibited from removal from opening (7164) unless bar code (7160) is suitably scanned. As shown in FIG. 18B, once a user desires to remove hatch door (7158), user may scan bar code (7160) with a suitable device. Scanning bar code (7160) may instruct latch assembly (7162) to unlock hatch door (7158) such that a user may remove hatch door (7158) to provide access to hollow interior (7155), as shown in FIG. 18C. Therefore, proximal body (7150) may be structurally robust during exemplary use, while still providing access to hollow interior (7155) for harvesting internal components.

Figures 19A, 19B, 19C:
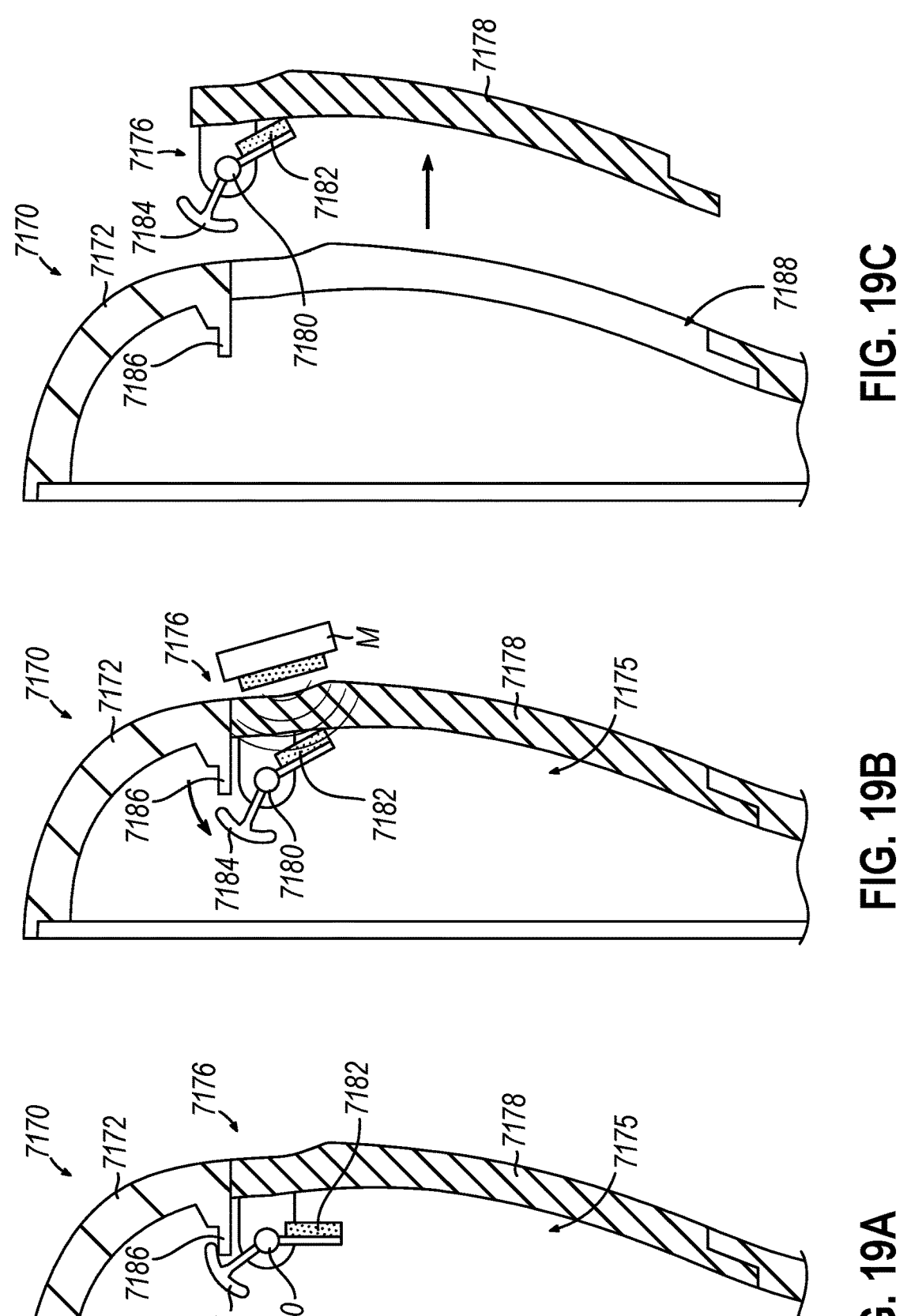
FIG. 19A depicts an enlarged sectional view of another exemplary proximal body that may be readily incorporated into any of the surgical instruments shown herein.
FIG. 19B depicts an enlarged sectional view of the proximal body of FIG. 19A, where a magnet is hovered over the proximal body.
FIG. 19C depicts an enlarged sectional view of the proximal body of FIG. 19A, where a hatch door of the proximal body is removed.

FIGS. 19A-19C show another exemplary proximal body (7170) that may be substantially similar to proximal body (7010, 7040, 7060, 7100, 7130, 7150) described above, with differences elaborated below. Therefore, proximal body (7170) includes sheath (7172) that may define a hollow interior (7165). Sheath (7172) includes a hatch assembly (7176) configured to provide suitable access to hollow interior (7175) in accordance with the description herein.

Hatch assembly (7176) includes a hatch door (7178) removably coupled to an opening (7188) defined by shroud (7172), a pivoting latch (7180) pivotally coupled with shroud (7172), and a locking protrusion (7186) within hollow interior (7175). Pivoting latch (7180) includes a magnet (7182) on one end and a latching body (7184) on the other end. Pivoting latch (7180) may be biased toward the locked position shown in FIG. 19A. In the locked position, pivoting latch (7180) may prevent hatch door (7178) from being removed from shroud (7172). If a user desires to remove hatch door (7178), user may wave a suitable magnet (M) over hatch door (7178), as shown in FIG. 19B. The magnetic attraction between magnet (M) and magnet (7182) may cause pivoting latch (7180) to pivot to an unlocked position, thereby allowing hatch door (7178) to be removed to provide access to hollow interior (7175), as shown in FIG. 19C. Therefore, proximal body (7170) may be structurally robust during exemplary use, while still providing access to hollow interior (7175) for harvesting internal components.

FIGS. 20A-20C show another exemplary proximal body (7190) that may be substantially similar to proximal body (7010, 7040, 7060, 7100, 7130, 7150, 7170) described above, with differences elaborated below. Therefore, proximal body (7190) includes sheath (7192) that may define a hollow interior (7195). Sheath (7192) includes a metal frame window (7196) configured to provide suitable access to hollow interior (7175) in accordance with the description herein. In particular, as shown in FIG. 20B, a user may expose metal frame window (7196) to a suitable heat source. Once metal frame window (7196) has a suitable amount of thermal energy, metal frame window (7196) may melt adjacent portions of sheath (7192), thereby creating a removable door (7198). As shown in FIG. 20C, door (7198) may then be removed to provide access to hollow interior (7195). Therefore, proximal body (7190) may be structurally robust during exemplary use, while still providing access to hollow interior (7195) for harvesting internal components.

Figures 21A, 21B, 21C:
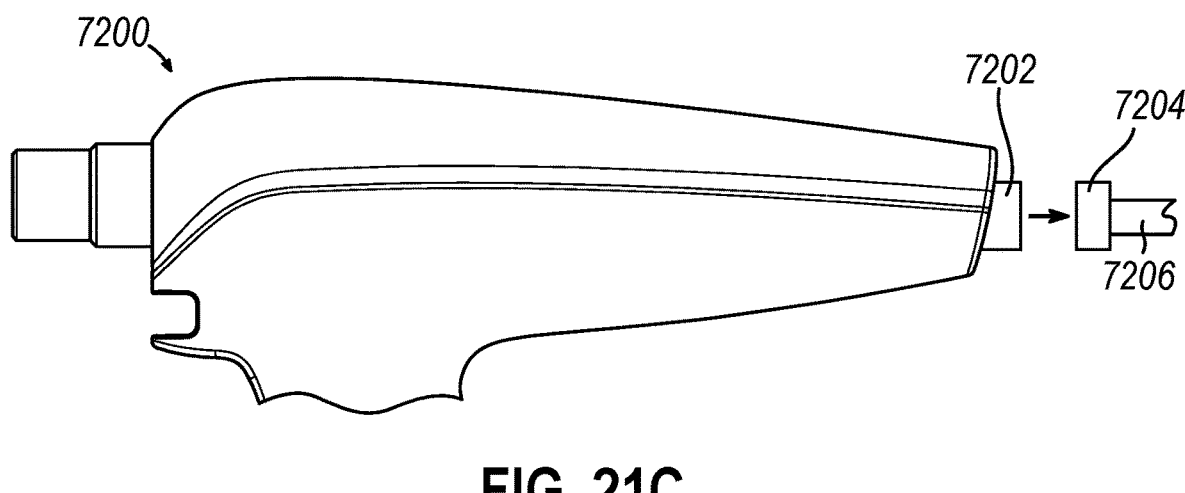
FIG. 21A depicts an enlarged elevational side view of another exemplary proximal body that may be readily incorporated into any of the surgical instruments shown herein.
FIG. 21B depicts an enlarged elevational side view of the proximal body of FIG. 21A, where an interactive is hovered over the proximal body.
FIG. 21C depicts an enlarged elevational side view of the proximal body of FIG. 21A, where a power cord is detached form the proximal body.

FIGS. 21A-21C show another exemplary proximal body (7200) that may be substantially similar to proximal body (7010, 7040, 7060, 7100, 7130, 7150, 7170, 7190) described above, with differences elaborated below. Proximal body (7200) also includes a power coupling (7202) which is configured to selectively electrically couple with a complementary power coupling feature (7204) of a power cord (7206). As best shown in FIGS. 21B-21C, power couplings (7202, 7204) are configured to remain coupled together unless the connection is severed with an interactive device (7208). Interactive device (7208) may be a physical key or an electrically activated release mechanism.

III. EXEMPLARY DISPOSAL BAGS FOR PROCESSING FEATURES OF USED SURGICAL INSTRUMENTS

As mentioned above, objects leaving the sterile field after a surgical procedure often require special consideration when processing for disposal, reuse, or remanufacturing. In some instances, a used surgical instrument may be disassembled into various predetermined categories and inserted within suitable transportation bags in order to transport disassembled surgical features for suitable processing. It may be desirable for transportation bags to be easily fillable, and/or inhibit emitting/leaking/spilling/transmitting biohazardous material contained within transportation bags while filled with features of a used surgical instruments. Further, it may be desirable for transportation bags to facilitate a determination of whether or not stored components may be suitable for reuse and/or remanufacturing.

FIGS. 22A-22D show an exemplary processing bag assembly (7210) that may be utilized to transmit used surgical features for suitable processing. Processing bag assembly (7210) is formed of a suitable processing bag (7212) that is configured to seal off stored surgical components from the external environment. Therefore, an internal surface of bag (7212) may be isolated from an external surface of bag (7212). Bag (7212) defines a sealable opening (7218) that may be selectively opened in order to place used surgical components (7215) into the interior of bag (7212), and then subsequently closed to create a seal such that surgical component (7215) are suitably isolated from the external environment.

As shown in FIGS. 22A-22C, bag assembly (7210) includes a pre-applied, closable, adhesive and/or tie element (7216) that enables the opening of bag assembly (7210) such that surgical components (7215) may be deposited into bag via sealable opening (7218). As shown in FIGS. 22C and 22D, adhesive and/or tie element (7216) is configured to re-close opening (7218) of bag (7212) in order to subsequently re-seal the interior of bag (7212) from the external environment. Any suitable type of adhesive and/or tie element may be utilized as would be apparent to one skilled in the art in view of the teachings herein.

Bag assembly (7210) also includes a biasing means (7214) located on or within a portion of bag (7212) adjacent to opening (7218). Biasing means (7214) may help bias opening (7218) toward the open position shown in FIGS. 22B-22C such that a user within the sterile environment may easily deposit used surgical components within bag (7212) without having to touch and/or contaminate the external surface of bag (7212). Biasing means (7214) may be suitably overcome in order to close opening (7218). Adhesive and/or tie element (7216) is sufficiently strong enough to overcome the bias of biasing means (7214) to close and seal opening (7218) for suitable transportation in accordance with the description herein.

Figures 23, 24, 25, 26:
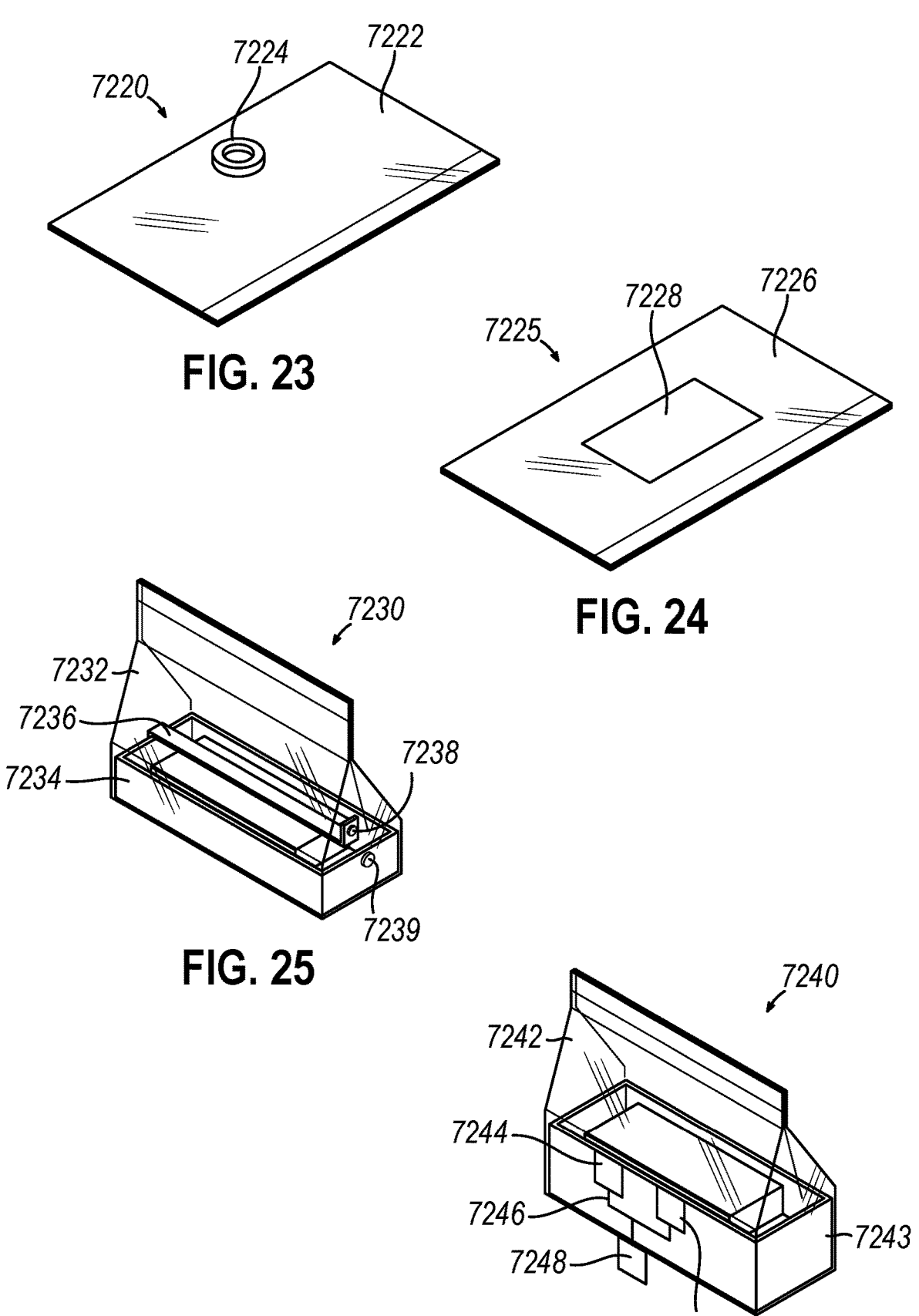
FIG. 23 depicts a schematic view of another exemplary processing bag assembly.
FIG. 24 depicts a schematic view of another exemplary processing bag assembly.
FIG. 25 depicts a schematic view of another exemplary processing bag assembly.
FIG. 26 depicts a schematic view of another exemplary processing bag assembly.

FIG. 23 shows another exemplary processing bag assembly (7220) that may be utilized to transmit used surgical features for suitable processing. Processing bag assembly (7220) may be substantially similar to processing bag assembly (7210) described above, with differences elaborated herein. Processing bag assembly (7220) includes a processing bag (7222) that may be substantially similar to processing bag (7212). Additionally, processing bag assembly (7220) includes a gas prevention/flammable control feature (7224) configured to fireproof and/or electrically isolate the interior of bag (7222). Gas prevention/flammable control feature (7224) may include any suitable structure as would be apparent to one skilled in the art in view of the teachings herein. For example, gas prevention/flammable control feature (7224) may include a valve configured to establish communication with a suction source to remove oxygen from the interior of bag (7222). As another example, gas prevention/flammable control feature (7224) may include a fire-retardant substance lining the interior of bag (7222).

FIG. 24 shows another exemplary processing bag assembly (7225) that may be utilized to transmit used surgical features for suitable processing. Processing bag assembly (7225) may be substantially similar to processing bag assembly (7210, 7220) described above, with differences elaborated herein. Processing bag assembly (7225) includes a processing bag (7225) that may be substantially similar to processing bag (7212, 7222). Additionally, processing bag assembly (7225) includes a set of instructions or indication of handling options (7228). For example, instructions or indication of handling options (7228) could include instructions for processing, or a warning of handling concerns for items that are intended to be sealed inside the bag. In some instances, bag (7226) could be color coded to indicate the processing path intended for items inside bag (7226).

FIG. 25 shows another exemplary processing bag assembly (7230) that may be utilized to transmit used surgical features for suitable processing. Processing bag assembly (7230) may be substantially similar to processing bag assembly (7210, 7220, 7225) described above, with differences elaborated herein. Processing bag assembly (7230) includes a processing bag (7232) that may be substantially similar to processing bag (7212, 7222, 7225). Additionally, processing bag assembly (7230) includes a rigid tray (7234) fixed within the interior of bag (7332). Tray (7234) may include complementary recesses dimensioned to receive specific portions of a used surgical instrument. Therefore, bag assembly (7230) may act as both a discrete holding frame and a sealing bag. Additionally, tray (7234) includes restraint snaps (7236) and restraining means (7238) that may be configured to further fix specific portions of used surgical instrument housed within tray (7234).

FIG. 26 shows another exemplary processing bag assembly (7240) that may be utilized to transmit used surgical features for suitable processing. Processing bag assembly (7240) may be substantially similar to processing bag assembly (7210, 7220, 7225, 7230) described above, with differences elaborated herein. Processing bag assembly (7240) includes a processing bag (7242) that may be substantially similar to processing bag (7212, 7222, 7225, 7232). Processing bag assembly (7240) also includes a tray (7243) that may be substantially similar to tray (7243) described above. Additionally, tray (7243) includes electrical connectors (7244) that are configured to establish electrical communication with specific portions of used surgical instrument housed within tray (7243). Electrical connectors (7244) are in communication with an external electrical coupling (7248) fixed to an exterior of bag (7242). After suitably loading portions of the used surgical instruments into tray (7243), a user may use a suitable electrical instrument to provide a small voltage or power to packaging via external electrical coupling (7248). The small voltage or power may travel to the electrical feature of used surgical instrument in communication with electrical connectors (7244) to check at least one functional aspect of the electrical feature to determine if there is capacity for reusing such an electrical feature.

Figure 27:
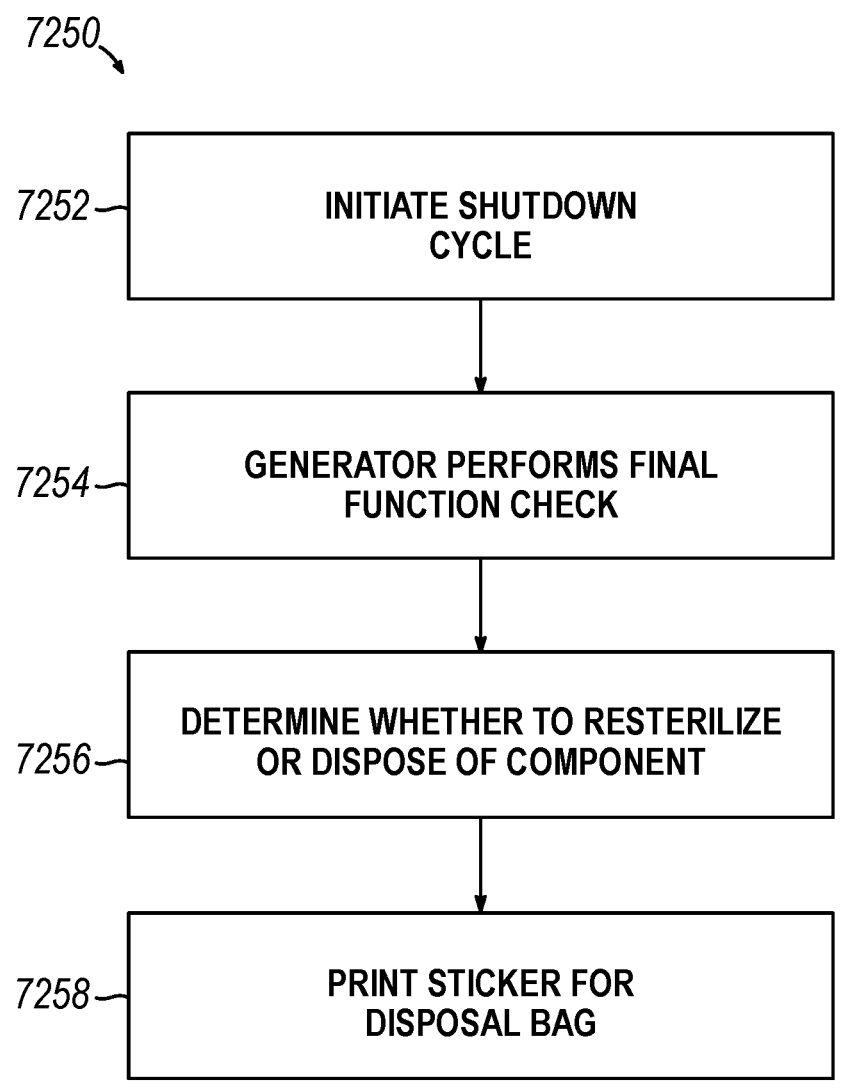
FIG. 27 depicts a flowchart of any exemplary shutdown cycle that may be used with any of the surgical instruments shown herein.

FIG. 27 shows an exemplary shutdown cycle (7250) that may be performed by generator module (140) or electronics of surgical instrument/tool (112, 117, 152, 154, 156) to check for potential recovery capacity and generate a sticker or label to be attached to processing bag (7212, 7222, 7225, 7232, 7242). First, after a user is finished using surgical instrument/tool (112, 117, 152, 154, 156) in accordance with the description herein, user may initiate (7252) the shutdown cycle. This initiation (7252) may be done using any suitable means as would be apparent to one skilled in the art in view of the teachings herein. Next, generator model (140) or electronics of surgical instrument/tool (112, 117, 152, 154, 156) may perform a final function check (7254) to determine if suitable components of surgical instrument/tool (112, 117, 152, 154, 156) have capacity for reuse. Next, generator model (140) or electronics of surgical instrument/tool (112, 117, 152, 154, 156) then determines (7256) whether features of surgical instrument/tool (112, 117, 152, 154, 156) should be sterilized or disposed of. Utilizing such determination, a printer may then print (7258) a sticker to be placed on processing bag (7212, 7222, 7225, 7232, 7242) which indicates the determination made above. Therefore, after exemplary use of surgical instrument/tool (112, 117, 152, 154, 156), a sticker may be generated and placed on processing bag (7212, 7222, 7225, 7232, 7242) to indicate the intended processing path for features of surgical instrument/tool (112, 117, 152, 154, 156).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector configured to transition between a deactivated configuration and an activated configuration, wherein the end effector is configured to transmit energy to tissue in the activated configuration; and (b) a proximal body operably attached to the end effector, wherein the proximal body comprises: (i) an electrical component configured to assist the end effector, (ii) a first shroud, (iii) a second shroud configured to couple with the first shroud to cooperatively define a hollow interior, wherein the electrical component is housed within the hollow interior, (iv) a first restraining feature associated with the first shroud, and (v) a second restraining feature associated with the second shroud, wherein the first and second restraining features are configured to couple together to cooperatively align the first shroud and the second shroud, wherein the first restraining feature and the second restraining feature are configured to selectively disengage to allow the first shroud and the second shroud to decouple from each other and expose the electrical component within the hollow interior.

Example 2

The surgical instrument of any one or more of the preceding Examples, wherein the first restraining feature comprises a resilient latch, wherein the second restraining feature comprises a locking shoulder.

Example 3

The surgical instrument of any one or more of the preceding Examples, wherein the resilient latch is configured to selectively disengage the locking shoulder to enable the first shroud and the second shroud to decouple.

Example 4

The surgical instrument of any one or more of the preceding Examples, wherein the second shroud defines an access hole configured to provide access to the resilient latch while the resilient latch is engaged with the locking shoulder.

Example 5

The surgical instrument of any one or more of the preceding Examples, wherein the first restraining feature and the second restraining feature are configured to couple by actuating in a vertical direction.

Example 6

The surgical instrument of any one or more of the preceding Examples, wherein the first restraining feature and the second restraining feature are configured to couple by actuating in a horizontal direction.

Example 7

The surgical instrument of any one or more of the preceding Examples, wherein the first restraining feature comprises a first magnet, wherein the second restraining feature comprises a second magnet.

Example 8

The surgical instrument of any one or more of the preceding Examples, wherein the first restraining feature and the second restraining feature are configured to couple together in a snap-fit fashion.

Example 9

The surgical instrument of any one or more of the preceding Examples, further comprising a biasing feature interposed between the electrical component and an interior of the second shroud.

Example 10

The surgical instrument of any one or more of the preceding Examples, wherein the biasing feature is configured to drive the electrical component away from the second shroud in response to the first shroud and the second shroud initially decoupling.

Example 11

The surgical instrument of any one or more of the preceding Examples, wherein the first restraining feature comprises a twist screw, wherein the second restraining feature comprises a female threaded sleeve.

Example 12

The surgical instrument of any one or more of the preceding Examples, wherein the proximal body comprises a handle.

Example 13

The surgical instrument of any one or more of the preceding Examples, further comprising a shaft assembly extending between the handle and the end effector.

Example 14

The surgical instrument of any one or more of the preceding Examples, wherein the end effector comprises an ultrasonic blade.

Example 15

The surgical instrument of any one or more of the preceding Examples, wherein the end effector comprises an electrode.

Example 16

The surgical instrument of any one or more of the preceding Examples, wherein the first and second restraining features are configured to prevent re-assembly of the proximal body when damaged.

Example 17

A surgical instrument, comprising: (a) an end effector configured to transition between a deactivated configuration and an activated configuration, wherein the end effector is configured to transmit energy to tissue in the activated configuration; and (b) a proximal body operably attached to the end effector, wherein the proximal body comprises: (i) an electrical component configured to assist the end effector, (ii) a first shroud, (iii) a second shroud configured to couple with the first shroud to cooperatively define a hollow interior, and (iv) a restraining feature comprising a latch configured to actuate between a locked position and an unlocked position, wherein the latch is configured to prevent the first shroud from disassociating with the second shroud in the locked position, wherein the latch is configured to allow the first shroud to disassemble with the second shroud in the unlocked position.

Example 18

The surgical instrument of any one or more of the preceding Examples, wherein the latch comprises a resilient leg configured to flex between the locked position and the unlocked position.

Example 19

A surgical instrument, comprising: (a) an end effector configured to transition between a deactivated configuration and an activated configuration, wherein the end effector is configured to transmit energy to tissue in the activated configuration; and (b) a proximal body operably attached to the end effector, wherein the proximal body comprises: (i) an electrical component configured to the end effector, (ii) a shroud assembly defining a hollow interior, (iii) a hatch door associated with the shroud, wherein the hatch door is configured to selectively disassociate with the shroud to expose the hollow interior, and (iv) a locking feature configured to selectively prevent the hatch door from disassociating with the shroud.

Example 20

The surgical instrument of any one or more of the preceding Examples, wherein the locking feature comprises a magnetic pivoting latch.

V. MISCELLANEOUS

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/854,065, entitled "Method of Reclaiming Portions of Surgical Instruments for Remanufacturing and Sustainability," filed on Jun. 20, 2022, published on U.S. Pat. Pub. No. 2024/0006048 on Jan. 4, 2024, the disclosure of which is incorporated by reference herein. Various suitable ways in which the teachings herein may be combined with the teachings of U.S. patent application Ser. No. 17/854,065 will be apparent to those of ordinary skill in the art in view of the teachings herein.

In addition to the foregoing, the teachings herein may be readily combined with the teachings of U.S. patent application Ser. No. 17/854,050, entitled "Surgical Instrument with Predetermined Separation Features for Waste Stream Utilization and Related Methods," filed on Jun. 20, 2022, published on U.S. Pat. Pub. No. 2024/0000474 on Jan. 4, 2024, the disclosure of which is incorporated by reference herein. Various suitable ways in which the teachings herein may be combined with the teachings of U.S. patent application Ser. No. 17/854,050 will be apparent to those of ordinary skill in the art in view of the teachings herein.

In addition to the foregoing, the teachings herein may be readily combined with the teachings of U.S. patent application Ser. No. 17/854,166, entitled "Surgical Instrument with Removable Cable and Associated Couplings," filed on Jun. 20, 2022, issued as U.S. Pat. No. 12,218,459 on Feb. 4, 2025, the disclosure of which is incorporated by reference herein. Various suitable ways in which the teachings herein may be combined with the teachings of U.S. patent application Ser. No. 17/854,166 will be apparent to those of ordinary skill in the art in view of the teachings herein.

In addition to the foregoing, the teachings herein may be readily combined with the teachings of U.S. patent application Ser. No. 17/854,641, entitled "Surgical System and Methods of Assembly and Disassembly of Surgical Instrument," filed on Jun. 20, 2022, issued as U.S. Pat. No. 12,490,999 on Dec. 9, 2025, the disclosure of which is incorporated by reference herein. Various suitable ways in which the teachings herein may be combined with the teachings of U.S. patent application Ser. No. 17/854,641 will be apparent to those of ordinary skill in the art in view of the teachings herein.

In addition to the foregoing, the teachings herein may be readily combined with the teachings of U.S. patent application Ser. No. 17/854,104, entitled "Robotic Surgical System with Removable Portion and Method of Disassembling Same," filed on Jun. 20, 2022, published as U.S. Pat. Pub. No. 2024/0000526 on Jan. 4, 2024, the disclosure of which is incorporated by reference herein. Various suitable ways in which the teachings herein may be combined with the teachings of U.S. patent application Ser. No. 17/854,104 will be apparent to those of ordinary skill in the art in view of the teachings herein.

In addition to the foregoing, the teachings herein may be readily combined with the teachings of U.S. patent application No. 17/854,110, entitled "System for Determining Disposal of Surgical Instrument and Related Methods," filed on Jun. 20, 2022, published as U.S. Pat. Pub. No. 2024/0001416 on Jan. 4, 2024, the disclosure of which is incorporated by reference herein. Various suitable ways in which the teachings herein may be combined with the teachings of U.S. patent application Ser. No. 17/854,110 will be apparent to those of ordinary skill in the art in view of the teachings herein.

In addition to the foregoing, the teachings herein may be readily combined with the teachings of U.S. patent application Ser. No. 17/854,114, entitled "Reclamation Packaging for Surgical Instrument and Related Methods," filed on Jun. 20, 2022, issued as U.S. Pat. No. 12,478,418 on Nov. 25, 2025, the disclosure of which is incorporated by reference herein. Various suitable ways in which the teachings herein may be combined with the teachings of U.S. patent application Ser. No. 17/854,114 will be apparent to those of ordinary skill in the art in view of the teachings herein.

In addition to the foregoing, the teachings herein may be readily combined with the teachings of U.S. patent application Ser. No. 17/854,127, entitled "Surgical System and Methods for Instrument Assessment and Cleaning," filed on Jun. 20, 2022, published as U.S. Pat. Pub. No. 2024/0003820 on Jan. 4, 2024, the disclosure of which is incorporated by reference herein. Various suitable ways in which the teachings herein may be combined with the teachings of U.S. patent application Ser. No. 17/854,127 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector configured to transition between a deactivated configuration and an activated configuration, wherein the end effector is configured to transmit energy to tissue in the activated configuration; and
   (b) a proximal body operably attached to the end effector, wherein the proximal body comprises:
      (i) an electrical component configured to the end effector,
      (ii) a shroud assembly defining a hollow interior,
      (iii) a hatch door associated with the shroud assembly, wherein the hatch door is configured to selectively disassociate with the shroud assembly to expose the hollow interior, and
      (iv) a locking feature configured to selectively prevent the hatch door from disassociating with the shroud assembly, wherein the locking feature comprises a metal frame window surrounding the hatch door, wherein the metal frame door is configured to accept an amount of thermal energy such that the metal frame door is configured to melt an adjacent portion of the shroud assembly to thereby allow the hatch door to disassociate with the shroud assembly.

2. The surgical instrument of claim 1, wherein the end effector comprises an ultrasonic blade.

3. The surgical instrument of claim 1, wherein the end effector comprises an electrode.

4. The surgical instrument of claim 1, wherein the shroud assembly comprises a first shroud and a second shroud configured to couple with the first shroud to cooperatively define the hollow interior.

5. The surgical instrument of claim 1, wherein the proximal body comprises a handle.

6. The surgical instrument of claim 5, further comprising a shaft assembly extending between the handle and the end effector.

* * * * *